US006900347B2

(12) United States Patent
Paulson et al.

(10) Patent No.: US 6,900,347 B2
(45) Date of Patent: May 31, 2005

(54) IMPURITY INHIBITION IN OLEFIN METATHESIS REACTIONS

(75) Inventors: Basil P. Paulson, Los Angeles, CA (US); Richard L Pederson, San Gabriel, CA (US)

(73) Assignee: Tilliechem, Inc., San Gabriel, CA (US)

( * ) Notice: Subject to any disclaimer, the term of this patent is extended or adjusted under 35 U.S.C. 154(b) by 375 days.

(21) Appl. No.: 10/155,854

(22) Filed: May 24, 2002

(65) Prior Publication Data

US 2003/0023123 A1 Jan. 30, 2003

Related U.S. Application Data

(63) Continuation-in-part of application No. 09/833,018, filed as application No. PCT/US00/31549 on Nov. 17, 2000, now Pat. No. 6,696,597, which is a continuation of application No. 09/387,486, filed on Sep. 1, 1999, now Pat. No. 6,215,019.
(60) Provisional application No. 60/293,931, filed on May 24, 2001, provisional application No. 60/166,543, filed on Nov. 18, 1999, and provisional application No. 60/098,792, filed on Sep. 1, 1998.

(51) Int. Cl.$^7$ .............................................. C07C 67/02
(52) U.S. Cl. ....................................... 560/261; 560/263
(58) Field of Search ................................. 560/261, 263

(56) References Cited

U.S. PATENT DOCUMENTS

| | | | |
|---|---|---|---|
| 3,721,718 A | 3/1973 | Hughes et al. .......... | 260/683 D |
| 4,844,916 A | 7/1989 | Ogawa et al. ............... | 424/409 |
| 4,923,119 A | 5/1990 | Yamamoto et al. ........... | 239/55 |
| 5,312,940 A | 5/1994 | Grubbs et al. ............... | 556/136 |
| 5,342,909 A | 8/1994 | Grubbs et al. ............... | 526/171 |
| 5,775,026 A | 7/1998 | Pearce et al. ................ | 43/124 |
| 5,831,108 A | 11/1998 | Grubbs et al. | |
| 5,916,983 A | 6/1999 | Pederson et al. ........... | 526/170 |
| 5,917,071 A | 6/1999 | Grubbs et al. ................ | 556/21 |
| 5,969,170 A | 10/1999 | Grubbs et al. ................ | 556/21 |
| 5,977,393 A | 11/1999 | Grubbs et al. ................ | 556/21 |
| 6,107,420 A | 8/2000 | Grubbs et al. ................ | 526/73 |
| 6,111,121 A | 8/2000 | Grubbs et al. ................ | 556/21 |
| 6,211,391 B1 | 4/2001 | Grubbs et al. ................ | 556/21 |
| 6,215,019 B1 | 4/2001 | Pederson et al. ........... | 560/234 |
| 6,225,488 B1 | 5/2001 | Mukerjee et al. ............. | 556/22 |
| 6,376,690 B1 | 4/2002 | Grubbs et al. ................ | 556/21 |

FOREIGN PATENT DOCUMENTS

| | | | | |
|---|---|---|---|---|
| WO | WO 96/04289 | 2/1996 | ........... | C07F/15/00 |
| WO | WO 98/39346 | 9/1998 | ........... | C07F/15/00 |
| WO | WO 99/00396 | 1/1999 | ........... | C07F/15/00 |
| WO | WO 99/00397 | 1/1999 | ........... | C07F/15/00 |
| WO | WO 99/28330 | 6/1999 | ........... | C07F/15/00 |
| WO | WO 99/29701 | 6/1999 | ........... | C07F/15/00 |
| WO | WO 99/50330 | 10/1999 | ........... | C08G/61/00 |
| WO | WO 99/51344 | 10/1999 | ........... | B01J/31/22 |
| WO | WO 00/15339 | 3/2000 | ........... | B01J/31/00 |
| WO | WO 00/43343 | 7/2000 | ........... | C07C/41/30 |
| WO | WO 00/58322 | 10/2000 | ........... | C07F/15/00 |
| WO | WO 00/71554 A2 | 11/2000 | ........... | C07F/15/00 |

OTHER PUBLICATIONS

Couturier, J.L. et al., *Angew. Chem. Int. Ed. Engl.* (1992) 31, 628, "A Cyclometalated Aryloxy(chloro)neopentylidene-tungsten Complex: A Highly Active and Stereoselective Catalyst for the Metathesis of cis– and trans–2–Pentene, Norbornene, 1–Methyl–norbornene, and Ethyl Oleate".

J.W. Ellis et al. *Inorg. Chem.* (1992) 31, 3026–3033, "Water-Soluble Tris(hydroxymethyl)phosphine Complexes with Nickel, Palladium, and Platinum, Crystal Structure of [Pd{P(CH$_2$OH)$_3$}$_4$]•CH$_3$OH".

N.J. Goodwin et al., *Chem. Commun.* (1996) 1551, FcCH$_2$P(CH$_2$ OH)$_2$: a new, reactive yet air–stable ferrocene-derived phosphine [Fc=(η•C$_5$H$_5$)FeC$_5$C$_5$H$_4$].

Grubbs et al., *Tetrahedron* (1998), 54, 4413–4450, "Recent Advances in Olefin Metathesis and Its Application in Organic Synthesis".

O'Leary,D.J. et al., *Tetrahedron Letters* (1998), 39, 7427, "A New Method for Cross–Metathesis of Terminal Olefins".

Scholl et al., *Organic Letters* (1999) 1, 953–956, "Synthesis and Activity of a New Generation of Ruthenium–Based Olefin Metathesis Catalysts Coordinated with 1,2–Dimesityl–4, 5–dihydro–imidazol–2–ylidene Ligands".

ApSimon, John, editor, "The Synthesis of Insect Pheromones, 1979–1989," The Total Synthesis of Natural Products, (John Wiley & Sons, 1992), pp. 252–265.

Blackwell, Helen E., et al., "New Approaches to Olefin Cross–Metathesis," 122 J. Am. Chem. Soc.(2000), pp. 58–71.

Brandsma, Lambert, Preparative Acetylenic Chemistry, 2nd ed. (Elsevier Science Publishers, 1988), pp. 176–177.

ISOM 1999 International Symposium Olefin Metathesis and Related Chemistry: Catalytic Processes for the Next Millenium, Jul. 11–15, 1999, The Netherlands, <http://web.mit.edu/rrs/isom/level2/contact.htm> (9 pages).

Laurence, Brian R., et al."erythro–6–Acetoxy–5–hexadecanolide, the Major Component of a Mosquito Oviposition Attractant Pheromone," 1 J. Chem. Soc. (Jan. 1, 1982), pp. 59–60.

Maynard, Heather D., et al. "Purification Technique for the Removal of Ruthenium from Olefin Metathesis Reaction Products," 40 Tetrahedron Letters (1999), pp. 4137–4140.

(Continued)

Primary Examiner—Paul J. Killos
(74) Attorney, Agent, or Firm—Stoel Rives LLP

(57) ABSTRACT

Reaction mixtures and methods using catalysts and reaction conditions to produce significantly improved yields (and thereby higher purity) of olefin metathesis products, with greatly reduced amounts of impurities. These techniques include in one instance reduction in temperature of reaction, and in another, the use of chemical compounds that act as reaction inhibitors of unwanted reactions to minimize or prevent formation of unwanted impurities.

48 Claims, 13 Drawing Sheets

OTHER PUBLICATIONS

Olagbemiro, Timothy O., et al., "Production of (5R, 6S)-6-Acetoxy-5-hexadecanolide, the Mosquito Oviposition Pheromone, from the Seed Oil of the Summer Cypress Plant, *Kochia scoparia* (Chenopodiaceae)," 47 J. Agric. Food Chem. (1999), pp. 3411–3415.

Schwab, Peter, et al., "Synthesis and Applications of RuCl2 (=CHR☐)(PR3)2: The Influence of the Alkylidene Moiety on Metathesis Activity," 118 J. Am. Chem Soc. (1996), pp. 100–110.

Shani, Arnon, "Integrated Pest Management Using Pheromones," 28 Chemtech 3 (Mar. 1998), pp. 30–35.

Coutrot, Ph., et al., "5–Formyl–δ–Valerolactone: A Useful Synthon for the Chiral Synthesis of the *Vespa Orientalis* Pheromone and the Mosquito Oviposition Attractant Pheromone," 35 Tetrahedron Letters 45 (1994), pp. 8381–8384.

Gravier–Pelletier, Christine, et al., "Enantiopure Hydroxylactones from L–Ascorbic and D–Isoascorbic Acids. Part II. Synthesis of (–)–(5R, 6S)–6–Acetoxy–5–Hexadecanolide and its Diastereomers," 51 Tetrahedron 6 (1995), pp. 1663–1674.

Howse, P.E., et al., *Insect Pheromones and their Use in Pest Management* (Chapman & Hall, 1998).

Dawson, G.W., et al., "Convenient Synthesis of Mosquito Oviposition Pheromone and a Highly Flourinated Analog Retaining Biological Activity," 16 J. Chem. Ecology 6 (1990), pp. 1779–1789.

Harris, M.K., et al., "Pecan Nut Casebearer (*Lepidoptera: pyralidae*) Sex Pheromone Used to Monitor Phenology and Estimate Effective Range of Traps," 90 J. Econ. Entomology (1997), pp. 983–987.

Henkel, B., "Lipase–Catalyzed Synthesis of (5R, 6S)–6–Acetoxyylkan–5–olides–Homologues of the Mosquito Oviposition Attractant Pheromone," 339 J. Prakt. Chem. (1997), pp. 434–440.

Laurence, B.R., et al., "Absolute Configuration of Mosquito Oviposition Attractant Pheromone 6–acetoxy–5–hexadecanolide," 11 J. Chem. Ecology 5 (1985), pp. 643–648.

Laurence, B.R. and Pickett, J.A., "An Oviposition Attractant Pheromone in Culex quinquefasciatus Say (*Diptera, culicidae*)," 75 Bull. Entomology Res. (1985), pp. 283–290.

Millar, J.G., "Degradation and Stabilization of E8,E10–Dodecadienol, the Major Component of the Sex Pheromone of the Codling Moth (*Lepidoptera, tortricidae*)," 88 J. Econ. Entomology 5 (Oct. 1995), pp. 1425–1432.

Millar, Jocelyn G., et al., "Sex Attractant Pheromone of the Pecan Nut Casebearer (*Lepidoptera: pyralidae*)" 4 Bioorganic & Medicinal Chemistry 3 (1996), pp. 331–339.

Negishi, Ei–ichi, et al., "Stereoselective Synthesis of Conjugated trans–Enynes Readily Convertible into Conjugated cis,trans–Dienes and its Application to the Synthesis of the Pheromone Bombykol," J.C.S. Chem. Comm. (1973), pp. 874–875.

Otieno, W.A., et al., "A Field Trial of the Synthetic Oviposition Pheromone with Culex quinquefasciatus Say (*Diptera, culicidae*) in Kenya," 78 Bull. Entomology Res. (1988), pp. 463–478.

Alexakis, A., et al.,"Z–1–Iodohexene," Organic Syntheses Collective vol. 7 (John Wiley & Sons, Inc., (1990), pp. 290–294.

Bach, R.D., and Knight, J.W., "Epoxidation of Olefins by Hydrogen Peroxide–Acetonitrile: cis–Cyclooctene Oxide," Organic Syntheses Collective vol. 7 (John Wiley & Sons, Inc., 1990), pp. 126–128.

Ruhoff, John R., "n–Heptanoic Acid," Organic Syntheses Collective vol. 2 (John Wiley & Sons, Inc., 1943), pp. 315–316.

Witzemann, E.J., et al., "dl–Glyceraldehyde Ethyl Acetal," Organic Syntheses Collective vol. 2 (John Wiley & Sons, Inc., 1943), pp. 307–309.

"Production By the U.S. Chemical Industry," C&EN (Jul. 4, 1994), p. 36.

Mori, Kenji, "Synthesis of Optically Active Pheromones," 45 Tetrahedron Report 11 (1989), pp. 3233–3298.

Svirskaya, P.I., et al., "Syntheses of Pure (9Z,11Z), (9E, 11E), (9Z,11Z), and (9Z,11E)–9,11—Hexadecadienals—Possible Candidate Pheromones," 10 Journal of Chemical Ecology 5 (1984), pp. 795–807.

Scholl, Matthias et al., *Organic Letters*, "Synthesis and Activity of a New Generation of Ruthenium–Based Olefin Metathesis Catalysts Corrdinated with 1,3–Dimesityl–4, 5–dihydroimidazol–2–ylidene Ligands", (1999) vol. 1, No. 6, 953–956.

(Trnka et al., *Acc. Chem Res.* 34:18–29 (2001)).

Arduengo et al., *Acc. Chem. Res.* 32:913–921 (1999).

Grayson, Martin, *Journal of American Chemical Society*, (Jan. 5, 1963) 79–83, "Phosphonium Compounds. III. Mechanism of Hydroxide Cleavage of Tetrakis(hydroxymethyl)phosphonium Chloride".

Bourissou et al. *Chem. Rev.* 100:39–91 (2000).

Corriu et al. *Chem. Commun.* 168–169 (1980).

Dervan et al. *J.Amer. Chem. Soc.* 98, 1265–1267 (1976).

Fürstner et al., *Angew. Chem., Int. Ed.* 39:3012–3043 (2000).

Huang et al., *J. Am. Chem. Soc.* 121:2674–2678 (1999).

Ivin et al., *J. Mol. Catal. A: Chem.* 133:1–16(1998).

Jafarpour et al., Organometallics 19 (11):2055–2057 (2000).

Randall et al., *J. Mol. Cat. A–Chem.* 133, 29–40 (1998).

Scholl et al., *Tetrahedron Letter* 40; 2247–22500 (1999).

Schwab et al., Angew, Chem., Int. Ed. Engl. 34:2039–2041 (1995).

Still, *J. Org. Chem.* 41, 3063 (1976).

"Efficient and Recyclable Monomeric and Dendritic Ru–Based Metathesis Catalysts," by Steven B. Garber, Jason S. Kingsbury, Brian L. Gray, and Amir H. Hoveyda; J. Am. Chem. Soc. 2000, 122, 8168–8179.

"A Recyclable Ru–Based Metathesis Catalyst," by Jason S. Kingsbury, Joseph P. A. Harrity, Peter J. Bonitatebus, Jr., and Amir H. Hoveyda; J. Am. Chem. 1999, 121, 791–799.

IMPURITY INHIBITION IN OLEFIN METATHESIS REACTIONS

STATEMENT OF RELATED APPLICATIONS

This application is a continuation in part and claims priority under 35 USC section 119(e) from U.S. Ser. No. 60/293,931 filed on May 24, 2001; and under 35 USC section 120 from U.S. Ser. No. 09/833,018 filed Apr. 10, 2001, which claims priority from PCT/US00/31549, filed Nov. 17, 2000, which in turn claims priority from both U.S. Ser. No. 60/166,543 filed Nov. 18, 1999 and is a continuation from U.S. Ser. No. 09/387,486 filed Sep. 1, 1999 (now issued as U.S. Pat. No. 6,215,019), which in turn claims priority from U.S. Ser. No. 60/098,792 filed Sep. 1, 1998.

BACKGROUND OF THE INVENTION

1. Technical Field

The invention relates to metathesis catalytic reaction processes that reduce the production of unwanted byproducts and significantly improve yield, and thereby purity, of the desired reaction products. In particular, the invention relates to catalysts, inhibitors and reaction conditions for olefin metathesis reactions.

2. Description of the Related Art

Over the past decade, olefin metathesis has emerged as a powerful carbon to carbon bond-forming reaction that is widely used in organic synthesis and polymer science (Trnka et al., *Acc. Chem. Res.* 34:18–29 (2001); Fürstner et al., *Angew. Chem., Int. Ed.* 39:3012–3043 (2000); Ivin et al., *J. Mol. Catal. A: Chem.* 133:1–16 (1998); Randall et al., *J. Mol. Catal. A: Chem.* 133:29–40 (1998); and Grubbs et al., *Tetrahedron* 54:4413–50 (1998)). In particular, the ruthenium carbene olefin metathesis catalysts, and derivatives thereof, have firmly established olefin metathesis as a versatile and reliable synthetic technique for advanced organic synthesis. The exceptionally wide scope of substrates and functional group tolerance makes olefin metathesis a valuable technique that quickly and efficiently produces otherwise hard to make molecules, compared to traditional synthetic organic techniques. Research efforts have enabled the elucidation of olefin metathesis reactions catalyzed by various transition metal complexes. In particular, certain ruthenium and osmium carbene compounds, known as "Grubbs catalysts", have been identified as effective catalysts for olefin metathesis reactions such as, for example, cross-metathesis (CM), ring-closing metathesis (RCM), ring-opening metathesis (ROM), ring-opening metathesis polymerization (ROMP), or acyclic diene metathesis (ADMET) polymerization. The metathesis reaction products have a variety of uses, for example synthesized insect pheromone products may be used as selectively targeted pest control agents in agriculture. Accordingly, there is considerable interest in improved reaction product yields and purity.

SUMMARY OF THE INVENTION

The present invention describes catalysts and reaction conditions to produce significantly improved yields (and thereby higher purity) of olefin metathesis products, with greatly reduced amounts of impurities. These techniques include in one instance reduction in temperature of reaction, and in another, the use of chemical compounds that act as reaction inhibitors of unwanted reactions to minimize or prevent formation of unwanted impurities.

The techniques of the invention are applicable to a wide range of metathesis reactions using a wide range of catalysts, including Grubbs, bis phosphine, and the like. The invention is useful in various cross-metathesis reactions, including but not limited to those that produce Peach Twig Borer pheromone, Omnivorous Leaf Roller pheromone, Tomato Pinworm pheromone, and 2-alkenal, acetates and alcohols. The invention is also useful in various ring-opening metathesis reactions, for example, to produce E-11-hexadecenyl acetate, Z-11-hexadecenyl acetate and Gypsy Moth pheromone; and in ring-closing various metathesis reactions, for example, to produce trifluoroacetyl protected N-3-pyrrolines.

Additional aspects and advantages of this invention will be apparent from the following detailed description of embodiments thereof, which proceeds with reference to the accompanying drawings.

BRIEF DESCRIPTION OF THE DRAWINGS

The following drawings illustrate specific examples of aspects of the invention as an aid to explaining the invention and do not in any way limit the scope of the invention as claimed herein.

DETAILED DESCRIPTION OF PREFERRED EMBODIMENTS

Figure 1:
FIG. 1 is a depiction of a metathesis reaction.

The present invention provides reaction conditions and chemical compound inhibitors that significantly improve product yields and purity in olefin metathesis reactions. The invention may be applied to any suitable metathesis catalyst reaction to obtain yield enhancement and impurity reduction.

As an initial matter, "olefin metathesis," as it is understood in the art, refers to the metal-catalyzed redistribution of carbon—carbon bonds in a reaction involving an olefin. While the invention is broadly applicable to almost all reactions involving olefin metathesis catalysts, some of these catalysts are better known than others. For example, over two decades of intensive research effort has culminated in the discovery of well-defined ruthenium and osmium carbenes, useful in the invention, that are highly active olefin metathesis catalysts and stable in the presence of a variety of functional groups. Among the catalysts of interest are the neutral ruthenium or osmium metal carbene complexes that possesses metal centers that are formally in the +2 oxidation state, have an electron count of 16, and are penta-coordinated. Other catalysts of particular interest include, but are not limited to, cationic ruthenium or osmium metal carbene complexes that possesses metal centers that are formally in the +2 oxidation state, have an electron count of 14, and are tetra-coordinated. Examples of such metathesis catalysts have been previously described in, for example, U.S. Pat. Nos. 5,312,940; 5,342,909; 5,831,108; 5,969,170; 6,111,121; 6,211,391; 5,917,071; 5,977,393; and 6,225,488 and PCT Publications WO 98/39346, WO 99/00396, WO 99/00397, WO 99/28330, WO 99/29701, WO 99/50330, WO 99/51344, WO 00/15339, WO 00/58322 and WO 00/71554, the disclosures of each of which are incorporated herein by reference to the extent relevant.

The ruthenium and osmium carbene complexes disclosed in these patents all possess metal centers that are formally in the +2 oxidation state, have an electron count of 16, and are penta-coordinated. These catalysts are of the general formula (I):

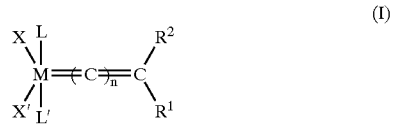

(I)

where n=0 to 2, M is a Group 8 transition metal such as ruthenium or osmium, X and X' are anionic ligands, L and L' are neutral electron donors, and R and R' are specific substituents, e.g., one may be H and the other may be a substituted silyl, substituted, or unsubstituted hydrocarbyl group such as phenyl or —C=C(CH$_3$)$_2$. Such complexes have been shown to be useful in catalyzing a variety of olefin metathesis reactions, including ring opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions. Their broad range of applications is due in large part to their excellent compatibility with various functional groups and relatively high tolerance to moisture, air, and other impurities (Schwab et al., Angew. Chem., Int. Ed. Engl. 34:2039–2041(1995); Schwab et al., J. Am. Chem. Soc. 118:100–110 (1996); Ivin, J. Mol. Cat. A-Chem. 133:1–16 (1998); Grubbs et al., Tetrahedron. 54:4413–4450(1998); and Randall et al., J. Mol. Cat. A-Chem. 133, 29–40 (1998)). However, as has been recognized by those in the field, the compounds display low thermal stability, decomposing at relatively low temperatures. Jafarpour et al., Organometallics 19(11):2055–2057 (2000).

For the most part, such metathesis catalysts have been prepared with phosphine ligands, e.g., tricyclohexylphosphine or tricyclopentylphosphine, exemplified by the well-defined, metathesis-active ruthenium alkylidene complexes (II) and (III):

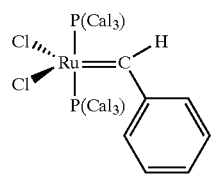

(II)

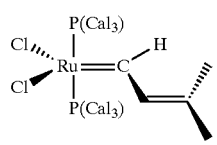

(III)

wherein "Cal" is a cycloalkyl group such as cyclohexyl or cyclopentyl. See Grubbs et al., U.S. Pat. No. 5,917,071 and Trnka et al., supra. To increase the reactivity of ruthenium-based catalysts, replacement of one of the phosphine ligands with a 1,3-disubstituted-4,5-dihydro-(4,5-disubstituted)-imidazole-2-ylidene, such as 1,3-dimesityl-4,5-dihydroimidazol-2-ylidene, furnishes more active catalysts due to a more electron-rich ruthenium metal center (Scholl et al., Tetrahedron Letter 40:2247–2200 (1999) and Scholl et al., Org. Lett. 1:953–956 (1999)).

From these studies, it became apparent that the highly basic N-heterocyclic carbene ligands, useful in the invention, are an excellent ligand set for improvement in olefin metathesis reactivity, and may be superior alternatives to phosphines (Trnka et al., supra; Bourissou et al. Chem. Rev. 100:39–91 (2000); Scholl et al., Tet. Lett. 40:2247–2200 (1999); Scholl et al., Organic Lett. 1(6):953–956 (1999); and Huang et al., J. Am. Chem. Soc. 121:2674–2678 (1999)). N-heterocyclic carbene ligands offer many advantages, including readily tunable steric bulk, vastly increased electron donor character, and compatibility with a variety of metal species. In addition, replacement of one of the phosphine ligands in these complexes significantly improves thermal stability. The vast majority of research on these carbene ligands has focused on their generation and isolation, a feat finally accomplished by Arduengo and coworkers within the last ten years (see, e.g., Arduengo et al., Acc. Chem. Res. 32:913–921 (1999)). Four representative second generation catalysts are the ruthenium complexes (IVA), (IVB), (VA) and (VB):

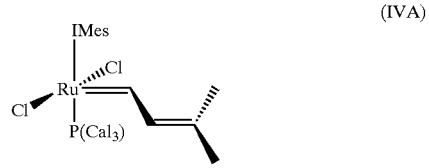

(IVA)

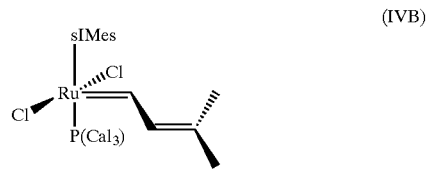

(IVB)

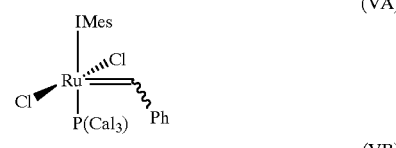

(VA)

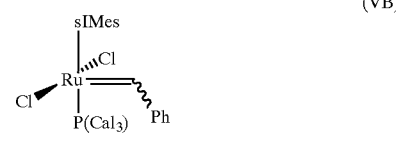

(VB)

In the above structures, "Cal" is as defined previously, "Ph" represents phenyl, "IMes" represents 1,3-dimesityl-imidazol-2-ylidene:

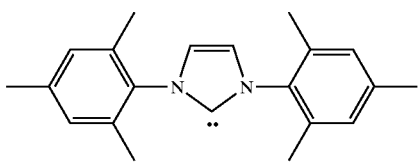

and "sIMes" represents 1,3-dimesityl-4,5-dihydroimidazol-2-ylidene:

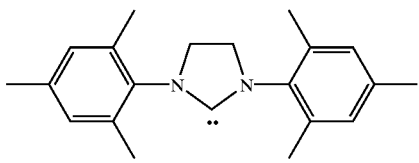

and "N-IMes" represents 1,3-dimesityl-triazolylidene:

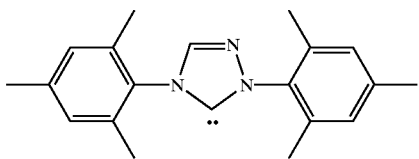

Other complexes formed from N-heterocyclic carbene ligands are also known. These transition metal carbene complexes, particularly those containing a ligand having the 4,5-dihydroimidazol-2-ylidene structure such as in sIMes, have been found to address a number of previously unsolved problems in olefin metathesis reactions, particularly cross-metathesis reactions.

All of the foregoing catalysts, and other olefin metathesis catalysts, may be used in accordance with the invention to obtain improved product yields and reduced impurity levels.

The prior art teaches that olefin metathesis catalysts must be heated for activation to initiate metathesis reactions. It has now been found that this approach generally renders the metathesis catalyst, including the second generation Grubbs catalysts (FIG. 10. Catalysts 848, 830, 627, and 884), too aggressive in their activity. It is theorized, without being bound that upon heating the catalysts will migrate the double bonds of the starting materials and reactions products to produce undesired impurities, thereby lowering product yields. If left unchecked, the double bond migration reaction will quickly proceed resulting in a reaction product containing about 30% or more impurities, and yield reaction products that are not commercially viable due to low yield of useful product and purifying costs.

To overcome this shortcoming, the invention, contrary to the prior art teaching, lowers the reaction temperature when an olefin metathesis catalyst is used. This results in some delay, of up to 7 hours, to initiate the metathesis reactions, but these reactions of the invention do not produce significant amounts of impurities and produce very close to the theoretical conversion (i.e. about 50% conversions of reaction mixtures containing equal moles of two reactants) to desired product. In the specification and claims, unless otherwise indicated, the term "yield" refers to reaction product and the term "conversion" refers to reactants consumed in the reaction. In particular, percent conversion is calculated by determining the amount (mass or moles) of a reactant consumed as a percentage of the amount (mass or moles) of that reactant initially present before reaction commenced. Since many metathesis reactions are equilibrium reactions, that do not go to a final endpoint consuming all reactants, but can nonetheless be driven to consuming all of one reactant by adding an excess of another reactant, the theoretical or calculated yield of reaction product is dependant on the proportions of reactants, if more than one olefin is present. Thus, for a reaction consuming equal molar amounts of two reactants, and where equal molar amounts of reactants are present, the yield may be derived from the conversion of either of the reactants. For example, if one mole of each reactant is needed to produce one mole of product, and in fact 0.8 moles of each reactant was consumed out of 1.2 moles of each initially present (either due to equilibrium, or due to stopping of the reaction), and 0.6 moles of product was produced, then the percent yield is 100(0.6/0.8)=75%. The percent conversion is 100(0.8/1.2)=66.67%. In the event one of the reactants is present in excess amounts to drive the reaction beyond the conversion achieved at equimolar amounts of the reactants, then conversion and yield are based on the reactant that is more consumed (i.e. has lowest initial amount present). For example, assume reactants A and B combine in equimolar amounts to form C, and there are 5.0 moles of reactant A and 2.5 moles of reactant B present before reaction. At equilibrium, after reaction, or when the reaction is stopped, there are 3.0 moles of A remaining and 0.5 moles of B (i.e. 2.0 moles of A were consumed) and 1.8 moles of C. Percent conversion of A is 100(2.0/2.5)=80%. Percent yield of C is 100(1.8/2.0)=90%. In a ring opening or ring closing reaction, where A converts to B, and one mole of A produces one mole of B. The percent conversion is 100(moles of A consumed/moles of A present before reaction). The percent yield is 100(moles of B produced/moles of A consumed). If no impurities are produced, the theoretical yield of 100% is achieved.

The invention provides yields that approach the theoretical yields quite closely. Thus, in accordance with the invention, in yield is within 10%, preferably 0 to 5% of the theoretically calculated yield. For example, if theoretical yield is 40% based on reactants consumed, then actual yield is better than 30% (within 10%), and is preferably better than 35%(within 5%).

The metathesis reactions are run neat (i.e. without solvent) to maximize reactor space efficiency. Using an excess of one starting material will increase the yield of product but decrease the time throughput yield.

In general, in accordance with the invention, reaction is carried out at a temperature that will produce a high yield, where a "high yield is a yield of about 40% or more, when using equal molar ratios of starting materials or a yield that is about 80% or more of the theoretical maximum. Thus, for the N-heterocyclic carbene Grubbs catalysts, useful temperatures are in the range from about −72° C. to about 20° C., and a temperature in the range about −5° C. to about 10° C., is better, since it is more easily achievable and reaction rates are useful. A temperature of less than about 10° C. is preferred, as is a temperature in the range about 5 to about 10° C.

In general, there is at least some inter relationship between temperature and yield: lower temperatures provide higher yields, but lowering temperature beyond a particular temperature (depending upon such factors as catalyst and reactants, for example) will at some point produce no further significant yield gain; i.e. there are diminishing yield gains. Further, a lower temperature reduces desired metathesis reaction rate as well, and requires longer batch reaction time. In addition, lower temperatures also delay reaction initiation (unless reaction is initiated at a higher temperature, and the reaction mixture is then cooled). So, there is a trade-off between (lower) reaction temperature, yield and reaction time.

In accordance with the invention, the temperature of a metathesis reaction using an s-IMes catalyst directly influences yield, and temperature reduction to about 0° C. results in about 50% conversion to desired product, i.e. insignificant amounts of impurity (i.e. a total of less than about 3 to about 5%). Of this total, less than 0.1% is the double bond migrated impurity (for example, 4-decenyl acetate or 6-decenyl acetate in the case of catalysts 716, 801, 823 and 835 in Example 1, below). These positional isomers are very different to remove from 5-decenyl acetate because these materials are liquids and difficult to recrystallize and their boiling points are very similar. The bulk of the remaining impurities (i.e. about 2.5%) is the 4- or 5-nonenyl acetate and 5- and 6-undecenyl acetate, which can be removed by careful vacuum distillation. [It is suspected but not proven that starting materials may contain about 2% to 3% 4-decene or 1,10-diacetoxy-4-decene, as impurities, which may account for the observed about 3% impurities.]

Figure 10:
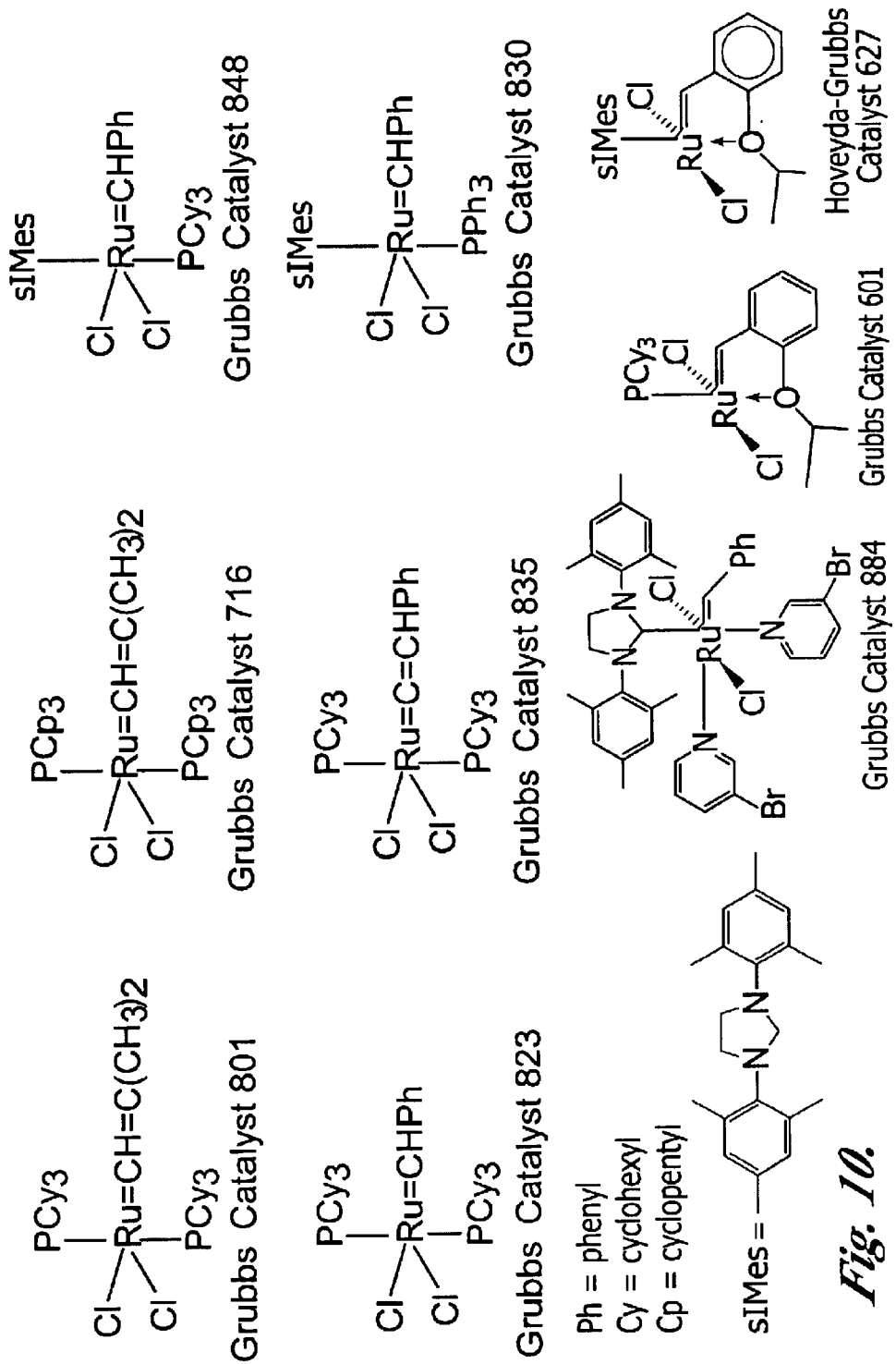
FIG. 10 is a depiction of formulae of certain metathesis catalysts.

The bis phosphine Grubbs catalysts (FIG. 10. Catalysts 801, 823, 716, and 601) are not as active as the s-IMes or IMes catalyst. These catalysts do not initiate appreciably at cold temperatures (e.g. less than about 10° C.) and usually require the reaction mixture to be warmed to 30° to 75° C. to obtain useful reaction rates. A disadvantage of warming the reaction mixture is that it increases the secondary reaction rate that produces impurities (these impurities are mainly double bond migrated species). In accordance with the invention, it has now been found that this (undesirable) secondary reaction rate is more sensitive to temperature than the metathesis reaction rate that produces desired product. In accordance with the invention, the secondary reaction rate is reduced to virtual insignificance by temperature reduction. In accordance with one aspect of the invention, bis phosphine catalyzed reaction mixtures are initially warmed to a range of temperatures that allow reaction initiation, and are then cooled to reduce the rates of reactions that produce byproducts that reduce product yield. Thus, in accordance with the invention, a bis phosphine catalyzed reaction mixture is optionally first heated to about 35° C. or more to initiate the reaction and is then cooled to the temperature range from about 0° C. to about 20° C., and better yet, to a temperature from about 5° C. to about 20° C. Preferably, the reaction mixture is cooled to less than about 10 to about 15° C.

In one aspect, the invention also provides chemical inhibitors of the reaction rates of the reactions that produce undesirable byproducts, also known as impurities. An impurity is regarded as present in an "insignificant" amount in accordance with the invention, if it is present in a small amount, and is relatively easily removed. When prior art metathesis reactions are carried out in a solvent free environment, for example not in a methylene chloride solution as is typically done, then there is typically the formation of a substantial amount of undesirable impurities such as double bond migrated impurities. These new compounds can undergo further metathesis reactions to produce a compound with 1-carbon less and 1-carbon more than the desired product. This process can repeat until an equilibrium mixture of impurities is obtained. According to one aspect of the invention, such impurities can be reduced or eliminated by adding an inhibitor selected from the electrophilic compounds, nucleophilic compounds and free radical scavengers (antioxidants). According to the invention, compounds that act as "metal hydride inhibitors", such as the halogenated alkanes and halogenated aromatics, for example, carbon tetrachloride, alpha, alpha dichlorotoluene, 1,2-dichloro ethane, 1,2-dibromoethane, bromoethane, bromopropane, bromobutane, etc., iodoethane, iodopropane, iodoobutane. etc. are useful inhibitors of metathesis reactions that produce such byproducts. Other useful inhibitors include antioxidants such as quinone, similar compounds to quinone such as BHT (butylated hydroxytoluene), Vitamin E as well as halogenated quinones and the like. Inhibitor dosage ranges from about 0.009 mol % to 5 mol %, typically 0.1 mol % based on the moles of reactant.

In general, the methathesis catalysts of most interest include, but are not limited to, neutral ruthenium or osmium metal carbene complexes that possesses metal centers that are formally in the +2 oxidation state, have an electron count of 16, are penta-coordinated, and are of the general formula I, shown below. Other catalysts of major interest include, but are not limited to, cationic ruthenium or osmium metal carbene complexes that possesses metal centers that are formally in the +2 oxidation state, have an electron count of 14, are tetra-coordinated, and are of the general formula II.

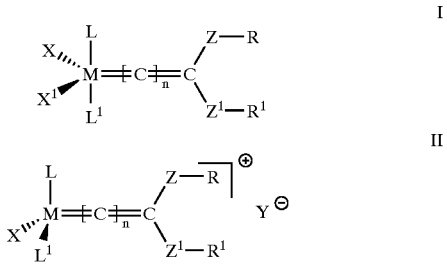

wherein:

M is ruthenium or osmium;

n is an integer between 0 and 5;

L and $L^1$ are each independently any neutral electron donor ligand;

R, $R^1$, and $R^2$ are each independently hydrogen or any hydrocarbyl or silyl moiety;

X and $X^1$ are each independently any anionic ligand;

Y is any non coordinating anion;

Z and $Z^1$ are each independently any linker selected from the group nil, —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, or —S(=O)$_2$—; and wherein any two or more of X, $X^1$, L, $L^1$, Z, $Z^1$, R, $R^1$, and $R^2$ may be optionally joined together to form a multidentate ligand and wherein any one or more of X, $X^1$, L, $L^1$, Z, $Z^1$, R, $R^1$, and $R^2$ may be optionally linked chemically to a solid or glassy support.

In preferred embodiments of these catalysts, L and $L^1$ are each independently selected from the group consisting of phosphine, sulfonated phosphine, phosphite, phosphinite, phosphonite, arsine, stilbine, ether, amine, amide, imine, sulfoxide, carbonyl, carboxyl, isocyanide, nitrosyl, pyridine, quinoline, thioether, and nucleophilic heterocyclic carbenes of the general formula III:

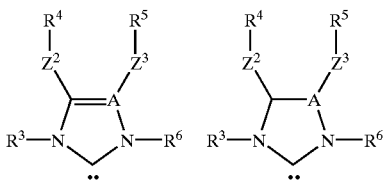

III wherein:
A is either carbon or nitrogen;
$R^3$, $R^4$, $R^5$, and $R^6$ are each independently hydrogen or any hydrocarbyl moiety, except that in the case where A is nitrogen $R^5$ is nil;
$Z^2$ and $Z^3$ are each independently any linker selected from the group nil, —O—, —S—, —$NR^2$—, —$PR^2$—, —P(=O)$R^2$—, —P(O$R^2$)—, —P(=O)(O$R^2$)—, C(=O)—, —C(=O)O—, —OC(=O)—, —OC(=O)O—, —S(=O)—, or —S(=O)$_2$—, except that in the case where A is nitrogen $Z^3$ is nil; and
$Z^2$, $Z^3$, $R^4$, and $R^5$ together may optionally form a cyclic optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In some catalysts of interest, L and $L^1$ are each a phosphine of the formula $PR^7R^8R^9$, where $R^7$, $R^8$, and $R^9$ are each independently any hydrocarbyl moiety, particularly aryl, primary $C_1$–$C_{10}$ alkyl, secondary alkyl or cycloalkyl. In certain other embodiments, L and $L^1$ are selected from the group consisting of —P(cyclohexyl)$_3$, —P(cyclopentyl)$_3$, —P(isopropyl)$_3$, —P(butyl)$_3$, and —P(phenyl)$_3$.

In the embodiments of most interest L is a phosphine and $L^1$ is a nucleophilic carbene of the general formula III. Preferably, L is selected from the group consisting of —P(cyclohexyl)$_3$, —P(cyclopentyl)$_3$, —P(isopropyl)$_3$, —P(butyl)$_3$, and —P(phenyl)$_3$ and $L^1$ is selected from the group consisting of:

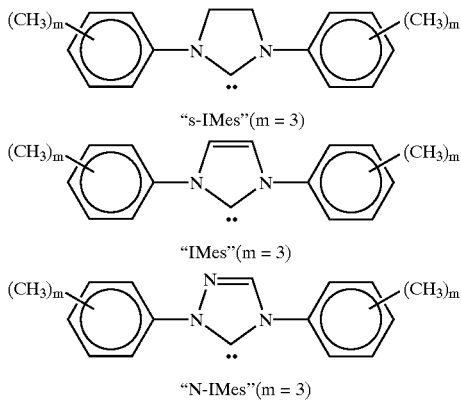

wherein m is an integer between 0 and 5.

Relating to R and $R^1$–$R^9$, examples of hydrocarbyl moieties include, but are not limited to, the group consisting of $C_1$–$C_{20}$ alkyl, $C_3$–$C_{20}$ cycloalkyl, $C_2$–$C_{20}$ alkenyl, $C_2$–$C_{20}$ alkynyl, aryl, heteroaryl, aralkyl, or alkaryl. Examples of silyl moieties include, but are not limited to, tri(hydrocarbyl)silyl, tri(hydrocarbyloxy)silyl, or mixed (hydrocarbyl) (hydrocarbyloxy)silyl. Optionally, each of the R, $R^1$ or $R^2$ substituent groups may be substituted with one or more hydrocarbyl or silyl moieties, which, in turn, may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In addition, any or all of R, $R^1$ and $R^2$ may be joined together to form a bridging or cyclic structure.

Also in addition, any or all of L, $L^1$, R, $R^1$ and $R^2$ may be joined to form a bridging or cyclic structure.

In embodiments of interest, the R substituent is hydrogen and the $R^1$ substituent is selected from the group consisting $C_1$–$C_{20}$ alkyl, $C_2$–$C_{20}$ alkenyl, aryl, alkaryl, aralkyl, trialkylsilyl, and trialkoxysilyl. In certain preferred embodiments, n equals 0, 1 or 2 and the $R^1$ substituent is phenyl, t-butyl or vinyl, optionally substituted with one or more moieties selected from the group consisting of $C_1$–$C_5$ alkyl, $C_1$–$C_5$ alkoxy, phenyl, and a functional group. In especially preferred embodiments, n equals 0 or 1 and $R^1$ is phenyl, t-butyl, or vinyl substituted with one or more moieties selected from the group consisting of chloride, bromide, iodide, fluoride, —$NO_2$, —$NMe_2$, methyl, methoxy and phenyl.

In some embodiments of interest, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthiol, aryl thiol, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthiol, aryl thiol, aryl, and $C_1$–$C_5$ alkyl sulfonate. In certain preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride, bromide, or iodide. In addition, the X and $X^1$ together may comprise a bidentate ligand.

Y may be derived from any tetra coordinated boron compound or any hexa coordinated phosphorus compound. Preferred boron compounds include $BF_4^-$, $BPh_4^-$, and fluorinated derivatives of $BPh_4^-$, but others are also useful. Preferred phosphorous compounds include, but are not limited to, $PF_6^-$ and $PO_4^{-2}$. The non-coordinating anion may be also any one of the following: $ClO_4^-$, $SO_4^=$, $NO_3^-$, $OTeF_5^-$, $F_3CSO_3^-$, $H_3CSO_3^-$, $CF_3COO^-$, $PhSO_3^-$, or $(CH_3)C_6H_5SO_3^-$. Y may be also derived from carboranes, chloro borates, carborane anions, fullerides, aluminoxanes, and the like.

The catalyst:olefin monomer ratio in the invention is preferably between about 1:1 and about 1:1,000,000. More preferably, the catalyst:olefin ratio is about 1:1 to 1:200, or conforms with the literature, which usually puts the ratio in the range between about 1:10 and about 1:10,000 and, most preferably, between about 1:20 and about 1:1,000 or about 1:20 to 1:100.

Particularly preferred metal catalysts include, but are not limited to: $(PCy_3)_2Cl_2Ru=CHPh$, $(PCy_3)_2Cl_2Ru=CH—CH=CMe_2$, $(PCy_3)_2Cl_2Ru=C=CHCMe_3$, $(PCy_3)_2Cl_2Ru=C=CHSiMe_3$, $(PCy_3)(s-IMes)Cl_2Ru=CH—CH=CMe_2$, $(PCp_3)_2Cl_2Ru=CH—CH=CMe_2$, $(PCp_3)_2Cl_2Ru=C=CHPh$, $(PCp_3)(s-IMes)Cl_2Ru=CH—CH=CMe_2$, $(PPh_3)(s-IMes)Cl_2Ru=C=CHCMe_3$, $(PPh_3)_2Cl_2Ru=C=CHSiMe_3$, $(PPh_3)_2Cl_2Ru=C=CHCMe_3$, $(P(i-Pr)_3)_2Cl_2Ru=C=CHPh$, $(PPh_3)(s-IMes)Cl_2Ru=C=CHSiMe_3$, $(PBu_3)_2Cl_2Ru=C=CHPh$, $(PPh_3)(s-IMes)Cl_2Ru=CH—CH=CMe_2$, $(PCy_3)(s-IMes)Cl_2Ru=C=CHPh$, $(PCp_3)(s-IMes)Cl_2Ru=C=CHPh$, $(PBu_3)(s-IMes)Cl_2Ru=C=CHPh$, $(PCy_3)(s-IMes)Cl_2Ru=CH—CH=CMe_2$, $(PBu_3)(s-IMes)Cl_2Ru=CH—CH=CMe_2$, $(PCy_3)(IMes)Cl_2Ru=CH—CH=CMe_2$, $(PCp_3)(IMes)Cl_2Ru=CH—CH=CMe_2$, $(PPh_3)(IMes)Cl_2Ru=C=CHCMe_3$, $(PPh_3)(IMes)Cl_2Ru=C=CHSiMe_3$, $(PPh_3)(IMes)Cl_2Ru=CH—CH=CMe_2$, $(PCy_3)(IMes)Cl_2Ru=C=CHPh$, $(PCp_3)(IMes)Cl_2Ru=C=CHPh$, $(PBu_3)(IMes)Cl_2Ru=C=CHPh$, $(PCy_3)(IMes)Cl_2Ru=CHPh$, $(PBu_3)(IMes)Cl_2Ru=CH—CH=CMe_2$, $(PCy_3)(IMes)Cl_2Ru=C=CHCMe_3$, $(PCy_3)ClRu=CHPh(o-O-Isop)$, $(PCp_3)ClRu=CHPh(o-O-Isop)$, $(PPh_3)ClRu=CHPh(o-O-Isop)$, $(PBu_3)ClRu=CHPh(o-O-Isop)$, $(s-IMes)ClRu=CHPh(o-O-Isop)$, $(IMes)ClRu=CHPh(o-O-Isop)$, $(N-s-IMes)ClRu=CHPh(o-O-Isop)$, and $(N-IMes)ClRu=CHPh(o-O-Isop)$. Where (o-O-Isop) is ortho-isopropoxyphenyl methylene.

For convenience and reference herein, various examples of metathesis catalysts (shown in FIG. 10) are identified by their molecular weight; ruthenium (II) dichloro(3-methyl-1,2-butenylidene)bis(tricyclopentylphosphine) (716); ruthenium (II) dichloro(3-methyl-1,2-butenylidene)bis (tricyclohexylphosphine) (801); ruthenium (II) dichloro (phenylmethylene)bis(tricyclohexylphosphine) (823); ruthenium (II) [1,3-bis-(2,4,6-trimethylphenyl)-2-imidazolidinylidene)dichloro(phenylmethylene) (tricyclohexylphosphine) (848); ruthenium (II) [1,3-bis-(2,4,6-trimethylphenyl)-2-imidazolidinylidene)dichloro(o-isopropoxyphenylmethylene) (627); ruthenium (II) [1,3-bis-(2,4,6-trimethylphenyl)-2-imidazolidinylidene)dichloro (phenylmethylene)(triphenylphosphine) (830), and ruthenium (II) dichloro(vinyl phenylmethylene)bis (tricyclohexylphosphine) (835); ruthenium (II) dichloro (tricyclohexylphosphine)(o-isopropoxyphenylmethylene) (601), and ruthenium (II) (1,3-bis-(2,4,6,-trimethylphenyl)-2-imidazolidinylidene)dichloro (phenylmethylene)(bis 3-bromopyridine (884)). This molecular weight-based nomenclature will be used the examples that follow.

The following examples merely serve to illustrate certain aspects of the invention for ease of explanation and are not to be construed as in any way limiting the scope of the invention as described and claimed herein.

EXAMPLES

In each of the Examples given herebelow, reference to "percent yield" of product should be interpreted as explained above. In general, when there are two reactants, since the metathesis reactions are equilibrium reactions, using equal molar ratios of symmetrical starting materials will produce a theoretical maximum of 50% product yield, if half of the reactants are consumed. The consumed moles of reactants could also produce byproducts, also referred to as impurities herein. Thus actual yield is less than theoretical, but approaches theoretical, in accordance with the invention.

Example 1

Screening Olefin Metathesis Catalysts for Activity and Impurity Profile

Grubbs olefin metathesis catalysts were screened for activity and impurity formation using the Argonaut Technologies (San Carlos, Calif.) FirstMate™ Manual Synthesizer. In the desired reaction, illustrated in FIG. 1, equal moles of 5-decene and 1, diacetoxy-5-decene are reacted to produce 5-decenyl acetate. Six large test tubes (2.22 cm ID×15.0 cm) were fitted to the FirstMate.™ Each test tube was filled with 1.67M 5-decene and 1.67M 1,10-diacetoxy-5-decene, in methylene chloride, to a final volume of 35 mL. The solutions were warmed to 45° C., under an inert gas, Argon. To each tube was charged one of the olefin metathesis catalysts 716, 801, 848, 823, 830, and 835 (0.117 mmol, 0.2 mol % catalyst), and mixing was initiated. Samples (~1 mL) of the reaction mixture were withdrawn from each tube, at times shown in Table 1, via a syringe and immediately quenched with 10 mL of 1 M trishydroxymethyl phosphine (THP) in isopropyl alcohol (IPA), shaken for 1 min and placed in a 65° C. oven for 1 hr. Water (5 mL) was added to each sample, shaken and the phases were allowed to separate. Three drops of the organic phase were added to separate 2 mL GC vials, diluted with IPA, and analyzed on a HP 5890 gas chromatograph (GC). Since the metathesis reactions are equilibrium reactions, using equal molar ratios of starting materials will produce a maximum of 50% yield. Thus, percent conversion is based on moles of product divided by moles of both reactants consumed in the reaction. The consumed moles of reactants also would produce byproducts or impurities. The results of the Percent Conversion in each reaction tube (i.e. for each catalyst) are shown in Table 1 and Percent Impurities are shown in Table 2.

TABLE 1

GC Percent Conversion to 5-Decenyl Acetate

| Catalyst | Time | | | |
|---|---|---|---|---|
| | 5 min | 30 min | 6 hr | 20 hr |
| 716 | 1.2 | 2.8 | 9.6 | 9.7 |
| 801 | 3.5 | 11.3 | 30.2 | 29.5 |
| 823 | 4.5 | 11.1 | 22.9 | 21.7 |
| 848 | 46.3 | 42.8 | 31.7 | 31.2 |
| 830 | 43.7 | 43.0 | 34.2 | 30.8 |
| 835 | 0.5 | | 0.5 | 0.5 |

TABLE 2

GC Percent Impurities Produced

| Catalyst | Time | | | |
|---|---|---|---|---|
| | 5 min | 30 min | 6 hr | 20 hr |
| 716 | 4.0 | 4.5 | 8.5 | 5.0 |
| 801 | 3.5 | 4.6 | 9.6 | 6.4 |
| 823 | 3.5 | 4.4 | 7.4 | 4.1 |
| 848 | 9.0 | 16.1 | 37.6 | 37.9 |
| 830 | 13.9 | 16.0 | 30.5 | 33.4 |
| 835 | 5.8 | | 7.0 | 3.3 |

These results indicate that catalysts 848 and 830 produce the highest yields of cross-methathesis product after 5 minutes; however, they also produce the greatest amount of impurities, with greater than 30% impurities formed after 6 hr. We were encouraged by the rapid reaction rate and set out to inhibit impurity formation while still retaining a fast reaction rate and high conversion.

Example 2

Cross-Methathesis Reaction with Catalyst 830 at −2° C.

The experiment as described in Example 1 was reproduced with 35 mL of 1.67 M 5-decene and 1.67 M 1,10- diacetoxy-5-decene in methylene chloride, using only catalyst 830 (0.117 mmol, 0.2 mol % catalyst). The reaction was carried out at a colder temperature, −2° C., under Argon. The results of the percent conversion and percent impurities are shown in Table 3.

TABLE 3

GC Results of Percent Conversion and Percent Impurities Produced using Catalyst 830 at −2° C.

| Time | % Conversion to 5-Decenyl Acetate | % Impurities Produced | % Impurities Detected |
|---|---|---|---|
| 0 min | 0.0 | 2.5* | 0 |
| 5 min | 0.8 | 4.7 | 0 |
| 15 min | 1.8 | 4.9 | 0 |
| 30 min | 20.5 | 6.9 | 0.8 |
| 1 hr | 43.5 | 7.3 | 1.7 |
| 2 hr | 46.6 | 7.5 | 1.8 |
| 8 hr | 44.90 | 11.1 | 2.4 |

*At t = 0 min, the sample was taken before Catalyst 830 was added. It has been observed that the metathesis catalyst removal technique introduces 2% to 4% impurity by GC. This impurity has been included in the Percent Impurties Detected column but subtracted out of the Impurities Produced column.

These results indicate that colder reaction temperatures slow the metathesis cross-coupling reaction but the reaction obtains close to theoretical conversion with 92% less impurities, compared to reactions run at elevated temperatures, see Table 2, 6 hour data point of 30.5% impurities compared with Table 3, 8 hour data point of 2.4% impurities.

Example 3

Cross-Metathesis Reaction with Metathesis Catalysts at 2–5° C.

The experiment as described in Example 1 was reproduced with 35 mL of neat 10.93 g (78.0 mmol) 5-decene and 20.0 g (78.0 mmol) 1,10-diacetoxy-5-decene. This time the reaction mixtures contained 0.2 mol % each of catalyst 848, 830 and 801, and reactions were run between 2° C. to 5° C., under Argon. Results of the percent conversion and percent impurities for catalysts 848, 830 and 801 are shown in Tables 4, 5 and 6 respectively.

TABLE 4

GC Results of Percent Conversion and Percent Impurities Produced using Catalyst 848 at 2° to 5° C.

| Time | % Conversion to 5-Decenyl acetate | % Impurities Produced | % Impurities Detected |
|---|---|---|---|
| 0 min | 0.0 | 0.9 | 0 |
| 30 min | 0.0 | 3.3 | 0 |
| 1 hr | 0.0 | 4.5 | 0 |
| 3.5 hr | 1.2 | — | — |
| 7 hr | 20.8 | 3.2 | 0.8 |
| 12 hr | 43.9 | 4.6 | 2.0 |
| 24 hr | 48.9 | 5.4 | 1.9 |

TABLE 5

GC Results of Percent Conversion and Percent Impurities Produced using Catalyst 830 at 2° to 5° C.

| Time | % Conversion to 5-Decenyl acetate | % Impurities Detected |
|---|---|---|
| 0 min | 0.0 | 0.9 |
| 30 min | 3.0 | — |
| 1 hr | 4.0 | — |
| 3.5 hr | 5.0 | — |
| 7 hr | 6.0 | — |
| 24 hr | 6.0 | — |

TABLE 6

GC Results of Percent Conversion and Percent Impurities Produced using Catalyst 801 at 2° to 5° C.

| Time | % Conversion to 5-Decenyl acetate | % Impurities Detected |
|---|---|---|
| 0 min | 0.0 | 0.9 |
| 30 min | 0.0 | — |
| 1 hr | 0.0 | — |
| 3.5 hr | 0.0 | — |
| 7 hr | 0.5 | — |
| 24 hr | 4.0 | — |

These results indicate that catalyst 848 initiated at low temperatures, without solvents and few impurities are produced at these lower temperature. Comparing 1 hr impurities of 4.5% at 0% conversion and 24 hr impurities of 5.4% at 48.9% conversion, less than 1% new impurities were produced by the metathesis catalyst. Catalyst 830 did not initiate without the presence of an organic solvent and catalyst 801 did not initiate presumably because the reaction temperature was too cold.

Example 4

Determination of the Impurity Profile when Operated Under Extended Reaction Times The following experiment determined the impurity profile after extended reaction times when run at −2° C. To a 20 mL round-bottomed flask was added 9 mL of neat 2.65 g (18.9 mmol) 5-decene and neat 4.8 g (18.9 mmol) 1,10-diacetoxy-5-decene, using (0.038 mmol, 0.2 mol %) catalyst 848, at −2° C. under Argon. The results of the percent conversion and percent impurities are shown in Table 7.

TABLE 7

GC Results of Percent Conversion and Percent Impurities Produced using Catalyst 848 at −2° C. for extended time.

| Time | 848% Conversion to 5-Decenyl acetate | % Impurities Produced | % Impurities Detected |
|---|---|---|---|
| 0 min | 0.0 | 0.9 | 0 |
| 6.75 hr | 3.0 | 1.6 | 0 |
| 18.15 hr | 38.8 | 3.4 | 0.9 |
| 27.15 hr | 46.0 | 4.8 | 0.9 |
| 41.0 hr | 47.3 | 5.4 | 1.6 |
| 61.5 hr | 48.1 | 4.8 | 1.7 |

These results indicate that running catalyst 848 under extended reaction times (i.e. 61.5 hr with 48.1% conversion) does not generate significantly greater amounts of impurities as compared to the impurity level at the 27.15 hr data point, with 46.0% conversion.

Example 5

Figure 2:
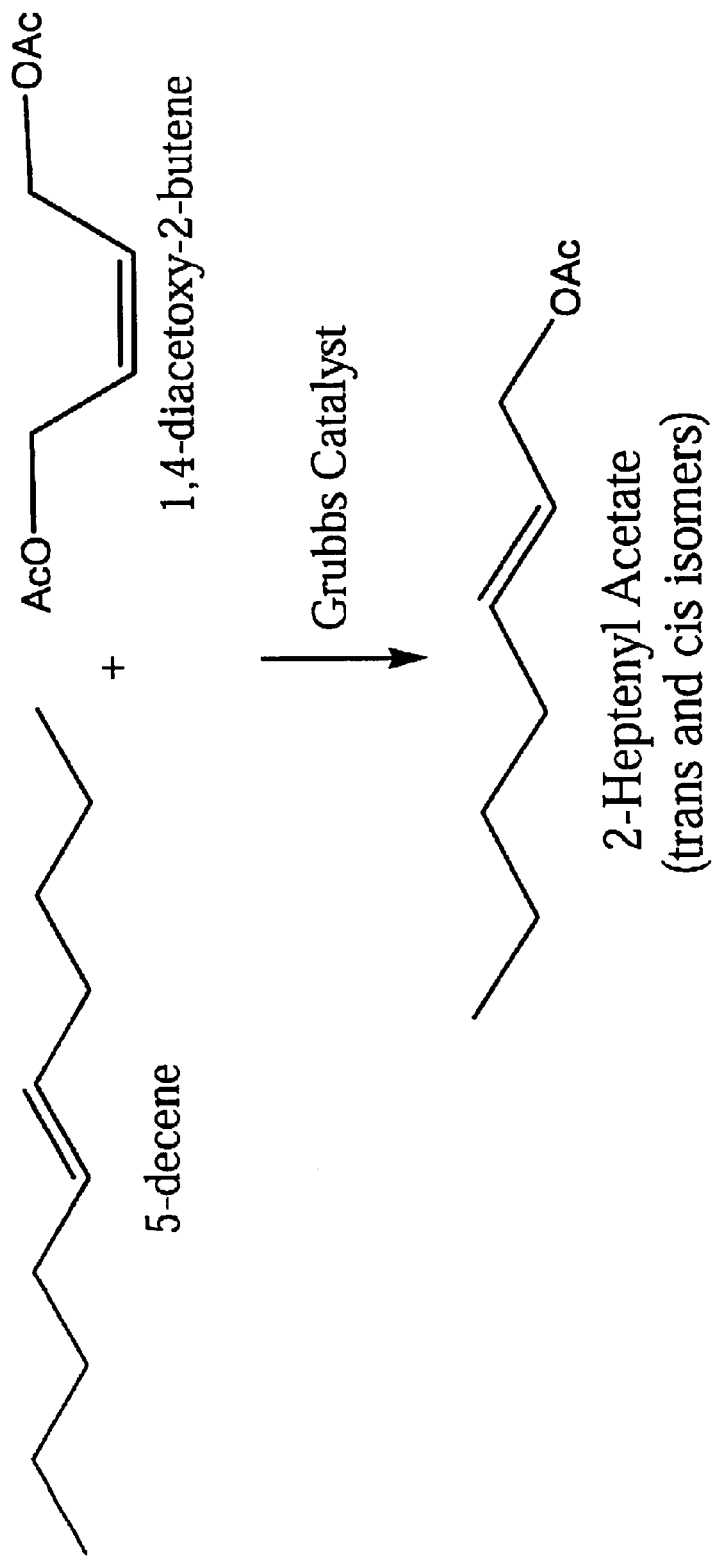
FIG. 2 is a depiction of a metathesis reaction.

Synthesis of 2-Heptenyl Acetate: Cross Metathesis of 5-Decene and 1,4-Diacetoxy-2-Butene This experiment was designed to synthesize 2-heptenyl acetate in accordance with FIG. 2. To a dry 50-mL round-bottomed flask was added 4 g (0.023 mol) 1,4-diacetoxy-2-butene, 3.3 g (0.023 mol) 5-decene and a magnetic stir bar. The solution was cooled to 0° C. and sparged with nitrogen for 10 minutes. Grubbs catalyst 848 (0.98 g, 1.2 mmol, 5 mol %) was added and the reaction was stirred at 0° C. for 24 hours. The reaction was quenched by addition of 15 ml of 2M THP in IPA solution, warmed to 60° C. with stirring for 24 hours. Water (5 mL) was added, stirred vigorously for 10 minutes, and phases separated. GC analysis of the organic phase indicated 25% 1,4-diacetoxy-2-butene, 25% 5-decene and 50% 2-heptenyl acetate; i.e., theoretical maximum yields were achieved.

Example 6

Figure 3:
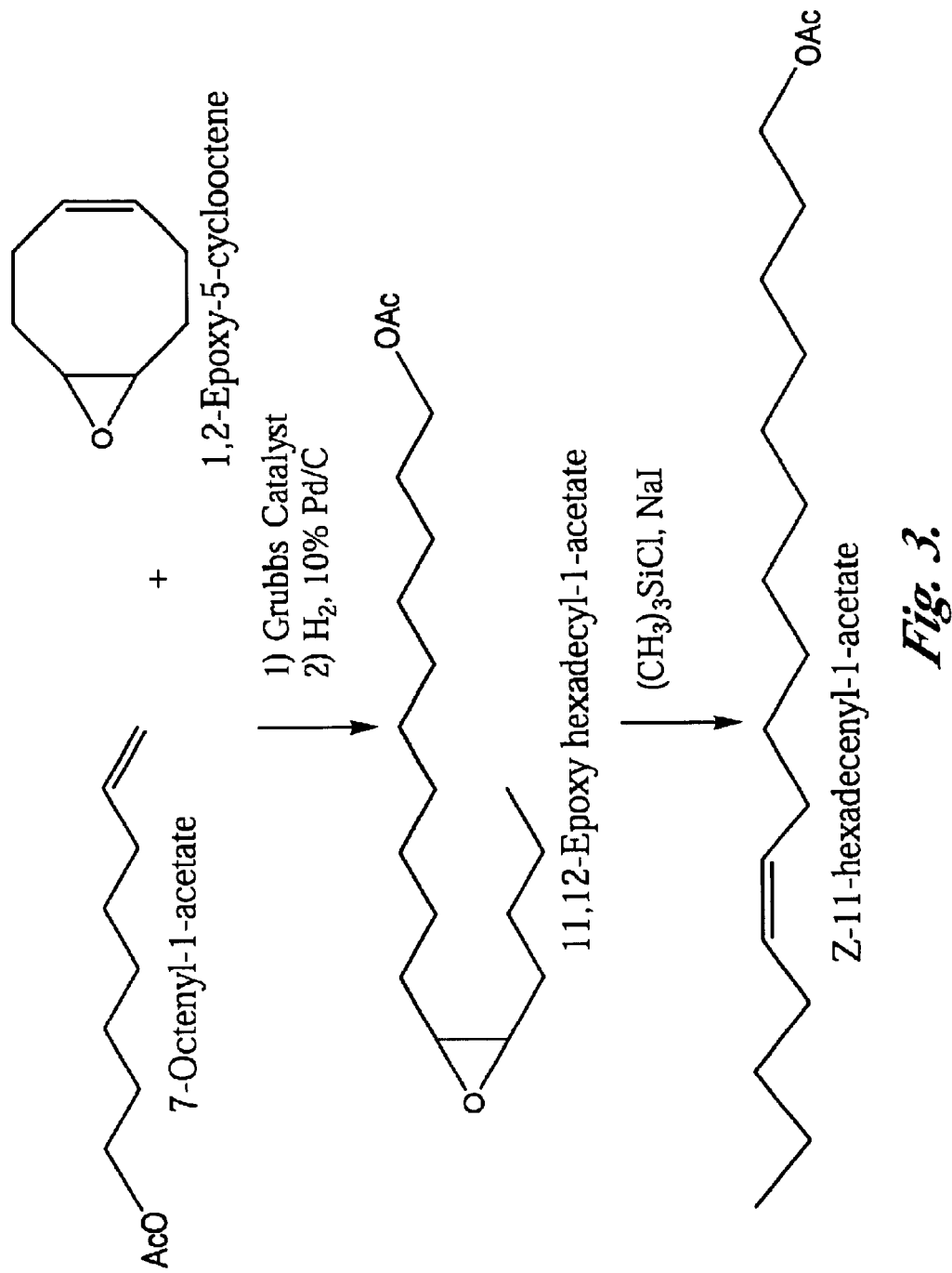
FIG. 3 is a depiction of a metathesis reaction.

Synthesis of Z-11-Hexadecenyl Acetate: Cross Metathesis of 7-Octenyl Acetate and 1.2-Epoxy-5-Cyclooctene This example is designed to produce Z-11-hexadecenyl acetate through the reaction shown in FIG. 3. To a dry 50-mL round-bottomed flask is added 4.5 g (0.026 mol) 7-octenyl acetate, 3.3 g (0.026 mol) 1,2-epoxy-5-cyclooctene and a magnetic stir bar. The solution is cooled to 0° C. and sparged with nitrogen for 10 minutes. Grubbs catalyst 848 (1.10 g, 1.30 mmol) is added and the reaction is stirred at 0° C. for 24 hours. The reaction is quenched by addition of 15 ml of 2M THP in IPA solution, warmed to 60° C. with stirring for 24 hours. Water (5 mL) is added and stirred vigorously for 10 minutes. The aqueous layer is separated, and the product washed with brine solution and dried over sodium sulfate. The product is purified by vacuum distillation, and then hydrogenated using 10% palladium on carbon (Pd/C) with a 5 psi overpressure of hydrogen. The catalyst is filtered off without further purification. The epoxide is converted to the cis olefin as described in (Tetrahedron Lett. 22, 3551 (1981)). There is sufficient detail to run the reaction 11,12-Epoxy-hexadecyl acetate is treated with 2.87 g (0.026 mol) chlorotrimethylsilane and 3.96 g (0.026 mol) sodium iodide. The reaction is slowly heated from room temperature to 60° C., until the starting materials are consumed. The mixture is then quenched with water and the organic phase was washed with an aqueous solution of sodium bicarbonate, and finally water. The organic phase is dried over sodium sulfate, acetylated with acetic anhydride and acetic acid and vacuum distilled to yield Z-11-hexadecenyl acetate.

Example 7

Figure 4:
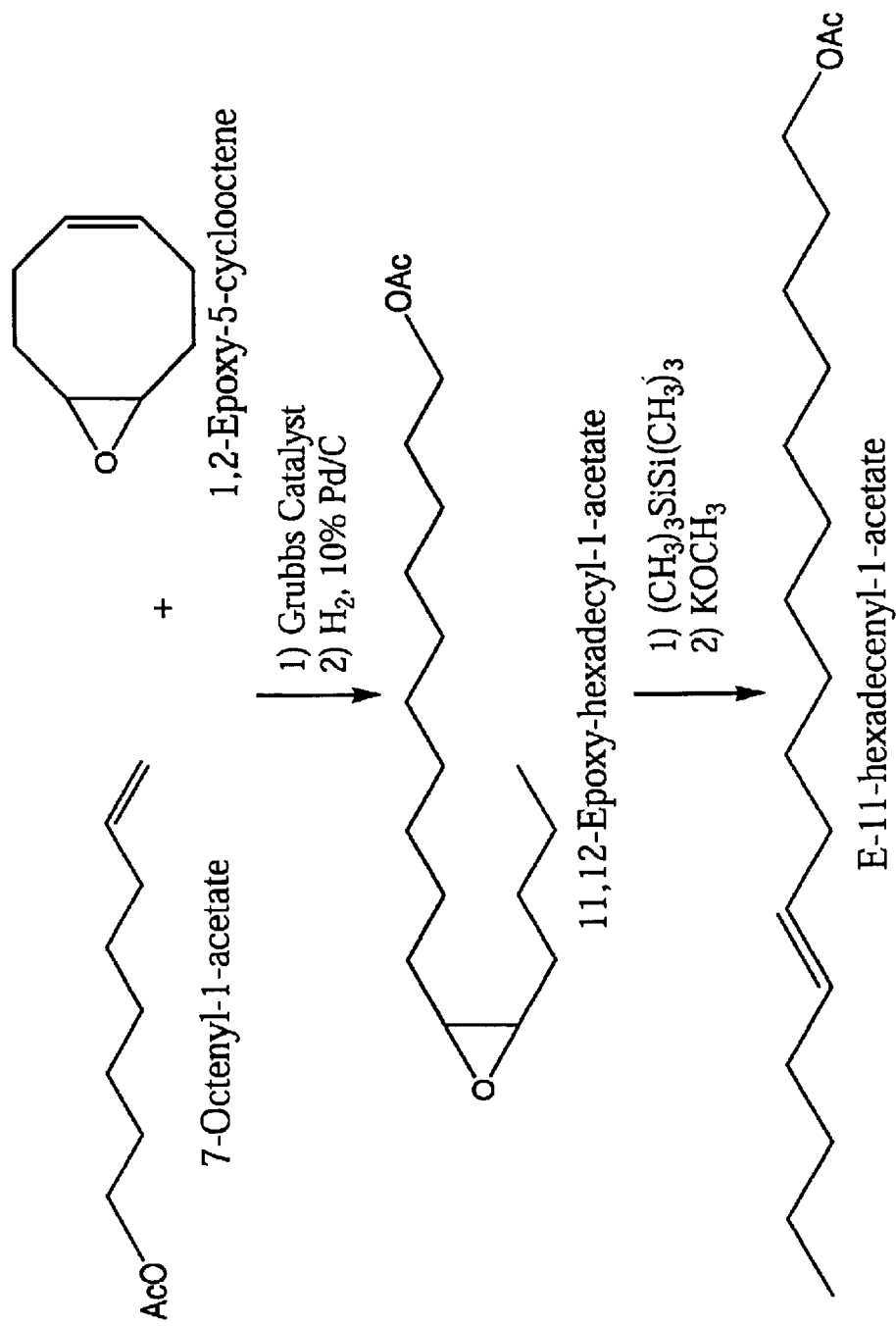
FIG. 4 is a depiction of a metathesis reaction.

Synthesis of E-11-Hexadecenyl Acetate: Cross Metathesis of 7-Octenyl Acetate and 1.2-Epoxy-5-Cyclooctene FIG. 4 shows the reaction path for producing E-11-hexdecenyl acetate. To a dry 50-mL round-bottomed flask is added 4.5 g (0.026 mol) 7-octenyl acetate, 3.3 g (0.026 mol) 1,2-epoxy-5-cyclooctene and a magnetic stir bar. The solution is cooled to 0° C. and sparged with nitrogen for 10 minutes. Grubbs catalyst 848 (1.12 g, 1.31 mmol) is added and the reaction is stirred at 0° C. for 24 hours. The reaction is quenched by addition of 15 ml of 2M THP in IPA solution, warmed to 60° C. with stirring for 24 hours. Water (5 mL) is added and stirred vigorously for 10 minutes. The aqueous layer is separated, and the product washed with brine solution and dried over sodium sulfate. The product is purified by vacuum distillation, and then hydrogenated using 10% palladium on carbon with a 5 psi overpressure of hydrogen. The catalyst is filtered off without further purification. The epoxide is converted to the trans olefin as described in J. Amer. Chem. Soc. 98, 1265 (1976); J. Org. Chem. 41, 3063 (1976); Chem. Commun. 168 (1980)). 11,12-Epoxy-hexadecyl acetate is treated with 3.87 g (0.026 mol) hexamethyldisilane and 3.34 g (0.026 mol) potassium methoxide at room temperature (about 25° C.). The solution is warmed to 50° C. and stirred until the starting materials are consumed. The mixture is quenched with water and the organic phase is washed with 1 M hydrochloric acid, saturated aqueous solution of sodium bicarbonate, and finally brine. The organic phase is dried over sodium sulfate and vacuum distilled to yield E-11-hexadecenyl acetate.

Example 8

Figure 5:
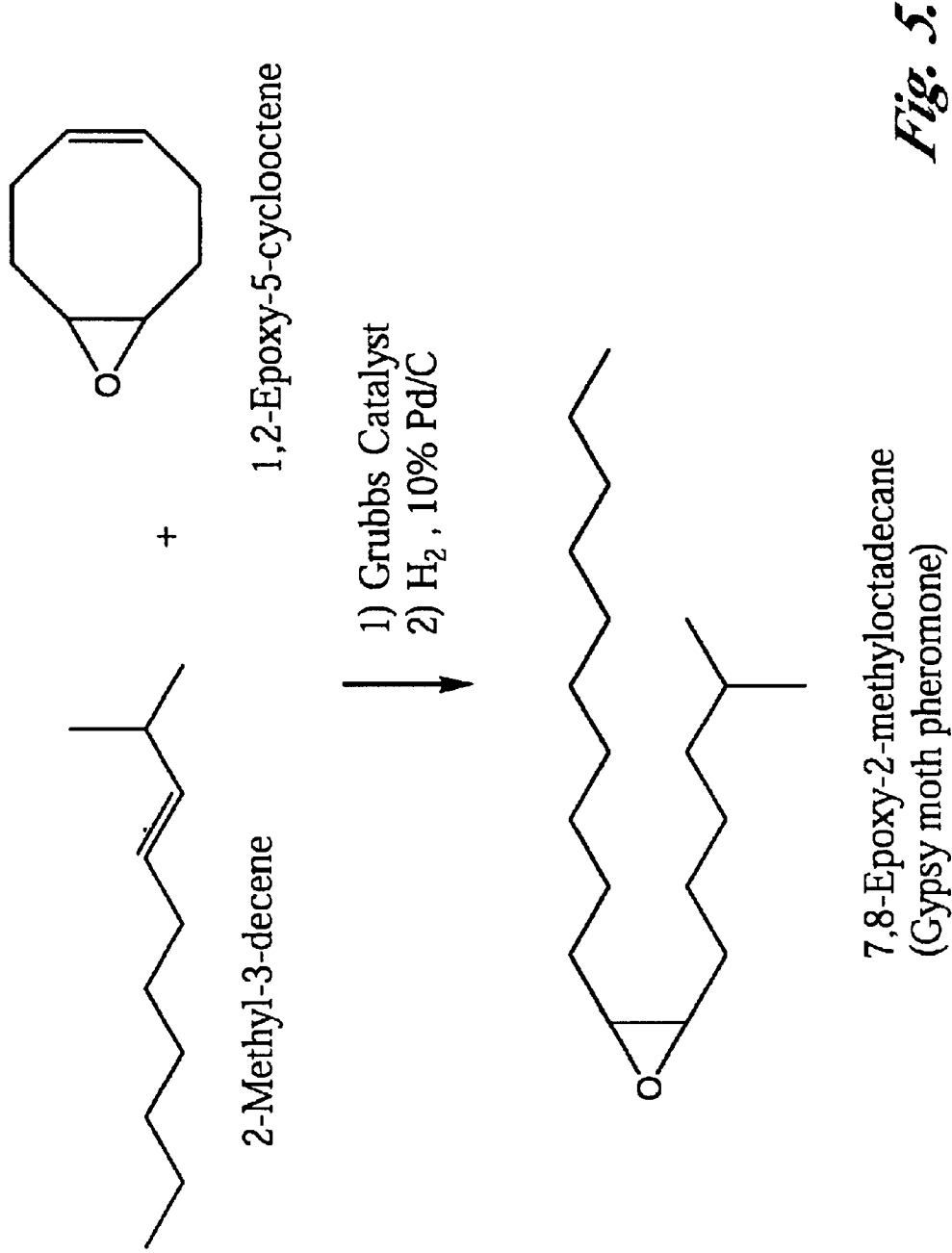
FIG. 5 is a depiction of a metathesis reaction.

Synthesis of Gypsy Moth Pheromone: 7,8-epoxy-2-methyl Octadecane by Cross Metathesis of 2-Methyl-3-Decene and 1.2-Epoxy-5-Cyclooctene The reaction for this example is shown in FIG. 5. To a dry 1-L round-bottomed flask is added 31.0 g (0.20 mol) 2-methyl-3-decene, 24.9 g (0.20 mol) 1,2-epoxy-5-cyclooctene and a magnetic stir bar. The solution is cooled to 0° C. and sparged with nitrogen for 10 minutes. Grubbs catalyst 848 8.5 g (1.0 mol) is added and the reaction was stirred at 0° C. for 24 hours. The reaction is quenched with 20 ml of 2M THP in IPA, warmed to 60° C. for 24 hours. The aqueous layer is separated, and the product washed with brine solution and dried over sodium sulfate. The product is purified by vacuum distillation, and then hydrogenated using 10% palladium on carbon with a 5 psi overpressure of hydrogen until the starting material is consumed. The catalyst is filtered off and the product is distilled under vacuum to yield the Gypsy moth pheromone.

Example 9

Cross-Metathesis of 1-Butene and 11-Eicosenyl Acetate

Figure 6:
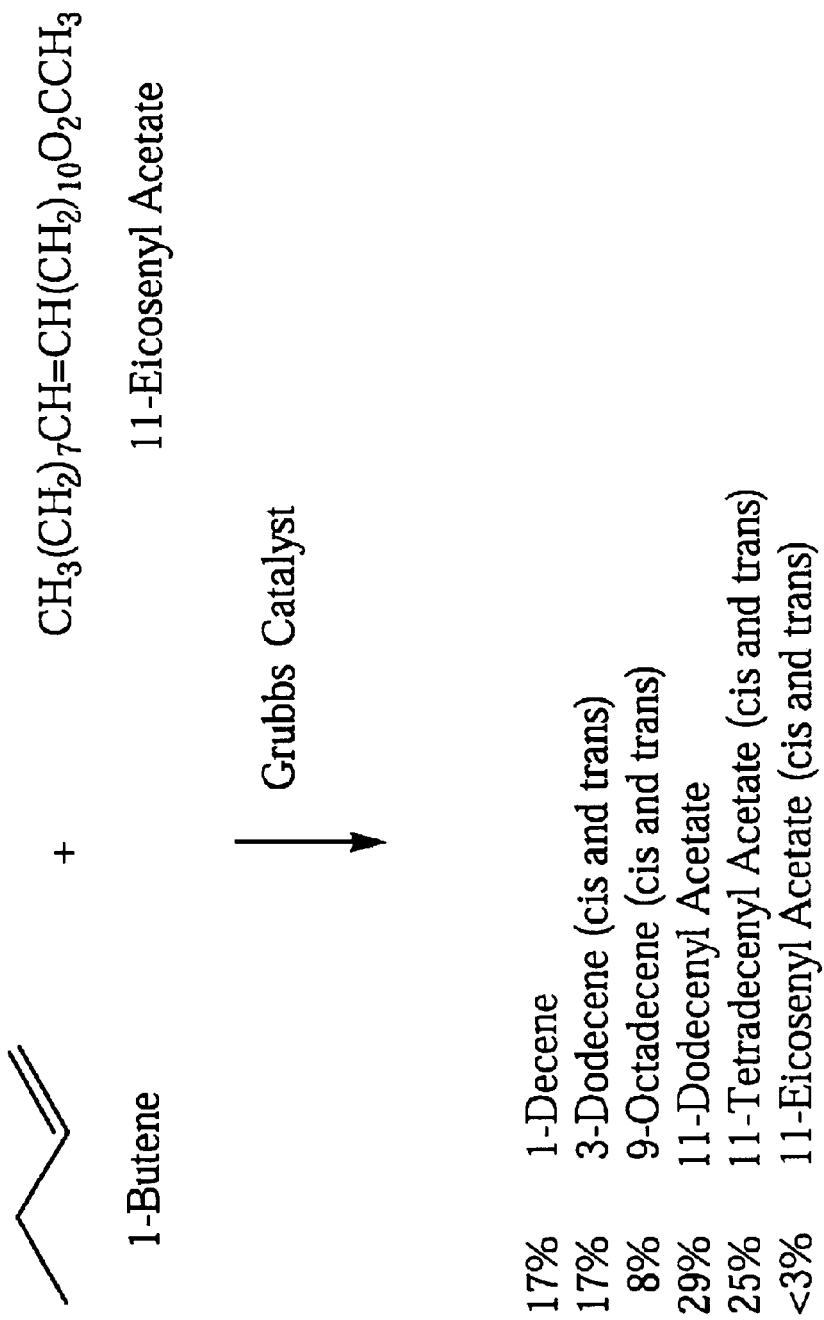
FIG. 6 is a depiction of a metathesis reaction.

The reaction for this example is shown in FIG. 6. To a dry 500-mL round-bottomed flask was added 50 g (0.15 mol) 11-eicosenyl acetate, and a magnetic stir bar. The vessel was cooled to 0° C. and sparged with nitrogen for 10 minutes. Grubbs catalyst 848 (6.3 g, 7.4 mmol) was added followed by 25 g (0.44 mol) liquefied 1-butene. The reaction was stirred at 0° C. for 24 hours. The reaction was quenched with 180 ml of 1 M THP in IPA, warmed to room temperature 24° C., and stirred for 24 hours. The aqueous layer was separated, and the product washed with brine solution and dried over sodium sulfate. Without further purification, the product was analyzed by GCMS to identify the mixture of products as described below: The products are characterized by comparing peaks with known standards, in conjunction with supporting data from mass spectrum analysis using a mass spectrum detector (GCMS-Agilent 5973N). Column: DB-225 30 m×0.25 mm (ID)×0.25 μm film thickness. Manufacturer: J&W; GC and column conditions:

Injector temperature: 250° C.
Oven temperature:
  Starting temperature: 40° C., hold time: 1 minute.
  Ramp rate 8° C./min to: 140° C., hold time: 5 minute.
  Ramp rate 20° C./min to: 210° C., hold time: 5 minute.
  Carrier gas: Helium.
Mean gas velocity: 31.3±3.5% cm/sec (calculated).
Split ratio: ~50:1.

These results demonstrate the catalyst 848 can catalyze disproportionation reactions to yield terminal olefin containing products.

Example 10

Figure 7:
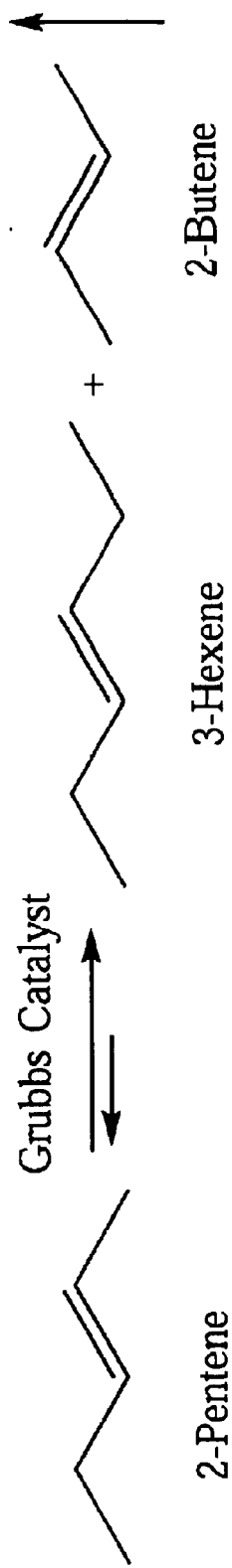
FIG. 7 is a depiction of a metathesis reaction.

Inhibitor Studies of Impurities Formed in the Cross-Metathesis of 2-Pentene to Yield 3-Hexene This example follows the reaction shown in FIG. 7., 2-Pentene (16 g, 230 mmol) was added to a dry 200 mL round-bottomed flask equipped with a condenser and a magnetic stir bar. The vessel was warmed to approximately 30° C. using an oil bath and sparged with nitrogen for 5 minutes. Grubbs' Catalyst 848 (8.5 mg, 0.01 mmol) was then added to the vessel.

Aliquots of reaction mixture were taken at 15-minute increments and analyzed by GC. Samples were analyzed by diluting two drops of the reaction mixture in methylene chloride and analyzed by GC. GC analysis was performed on a HP5890 GC with FID detector, equipped with a capillary GC column, DB-220™ (30 m×25 mm ID×25 um) column (GC method: 40° C. for 1 min then 8° C./min to 118° C. The area percent of each peak or group of peaks were tabulated directly without correction for differences in response.

Figure 11:
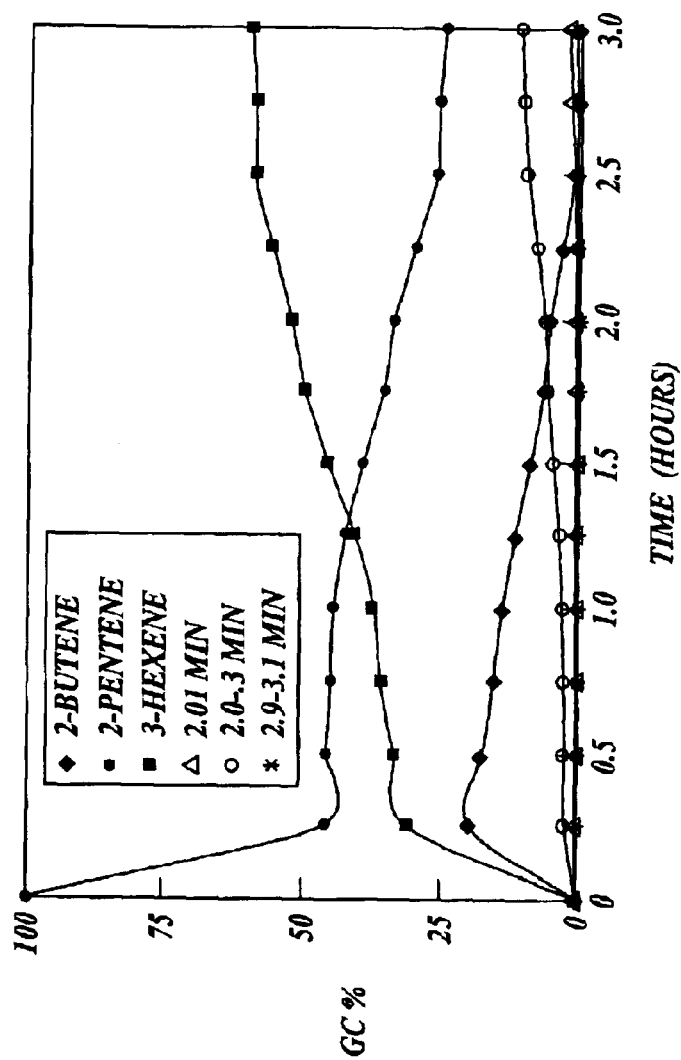
FIG. 11 is a graphical representation of analysis (by yield percent through gas chromatography, on the y-axis) versus time (x-axis) of a reaction mixture.
Figure 12:
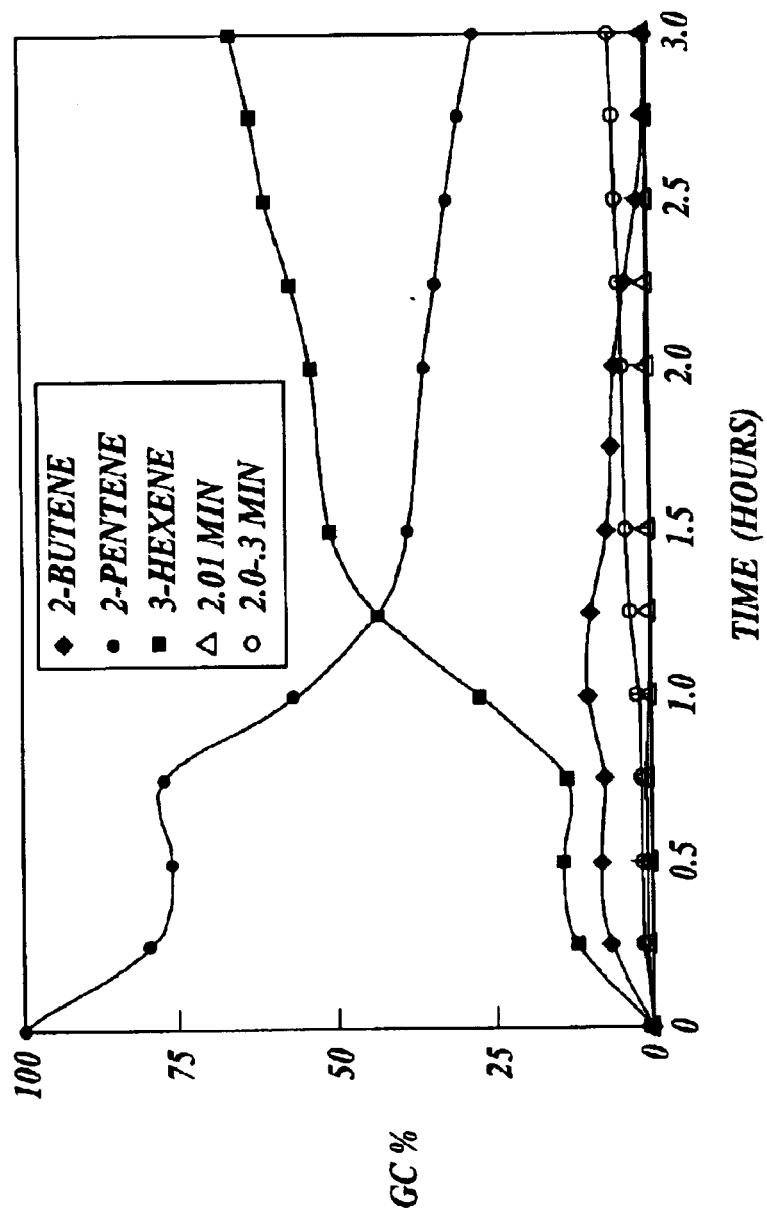
FIG. 12 is a graphical representation of analysis (by yield percent through gas chromatography, on the y-axis) versus time (x-axis) of a reaction mixture.
Figure 13:
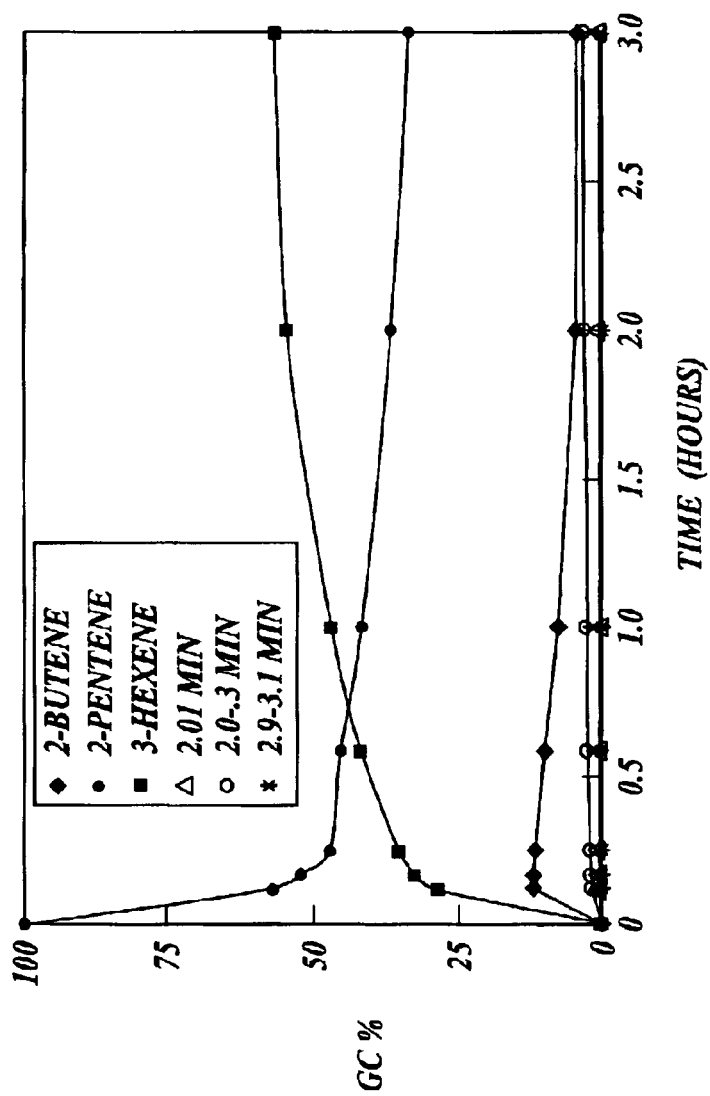
FIG. 13 is a graphical representation of analysis (by yield percent through gas chromatography, on the y-axis) versus time (x-axis) of a reaction mixture.

During these reactions, the temperature was raised slowly to remove 2-butene without losing 2-pentene. The results are displayed in FIGS. 11, 12 and 13. In the control experiment, FIG. 11, the amount of impurities grew steadily to 14% of the reaction mixture after 3 hr. Experiments with the addition of quinone (8.6 mol %) (FIG. 12) and 1-bromo-3-chloropropane (5.0 mol %) (FIG. 13) reduced the amount of impurities to 6% and 3%, respectively, while still obtaining about 60% product after three hours. These reactions demonstrate that 1-bromo-3-chloropropane, quinone and related compounds inhibit impurity formation and yield a commercially valuable product.

Example 11

Figure 8:
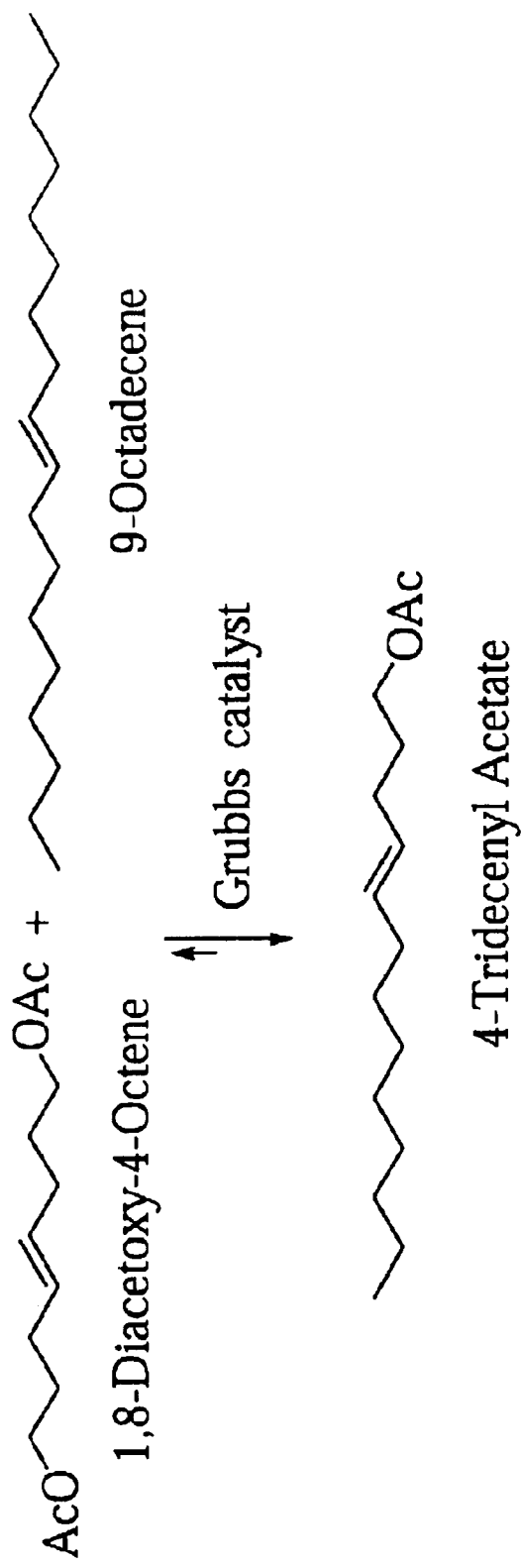
FIG. 8 is a depiction of a metathesis reaction.

Synthesis of Tomato Pinworm Pheromone (4-Tridecenyl Acetate): by Cross Metathesis of 1,8-Diacetoxy-4-Octene and 9-Octadecene The reaction is shown in FIG. 8. To a dry 500 mL round-bottomed flask was added 160.0 g (0.70 mol) 1,8-diacetoxy-4-octene, 176.0 g (0.70 mol) 9-octadecene and a magnetic stir bar. The solution was cooled to 0° C. and sparged with nitrogen for 20 minutes. Grubbs catalyst 848 1.48 g (0.18 mol %) was added and the reaction was stirred at 0° C. for 24 hours. The reaction was quenched with 25 ml of 2M THP in IPA, warmed to 60° C. for 12 hours. Water (100 mL) was added and stirred vigorously for 30 minutes. The aqueous layer was separated, and the product washed with brine solution and dried over sodium sulfate. GC analysis of the reaction mixture indicated normalized values of 25% 1,8-diacetoxy-4-octene, 25% 9-octadecene and 50% 4-tridecenyl acetate.

Example 12

Figure 9:
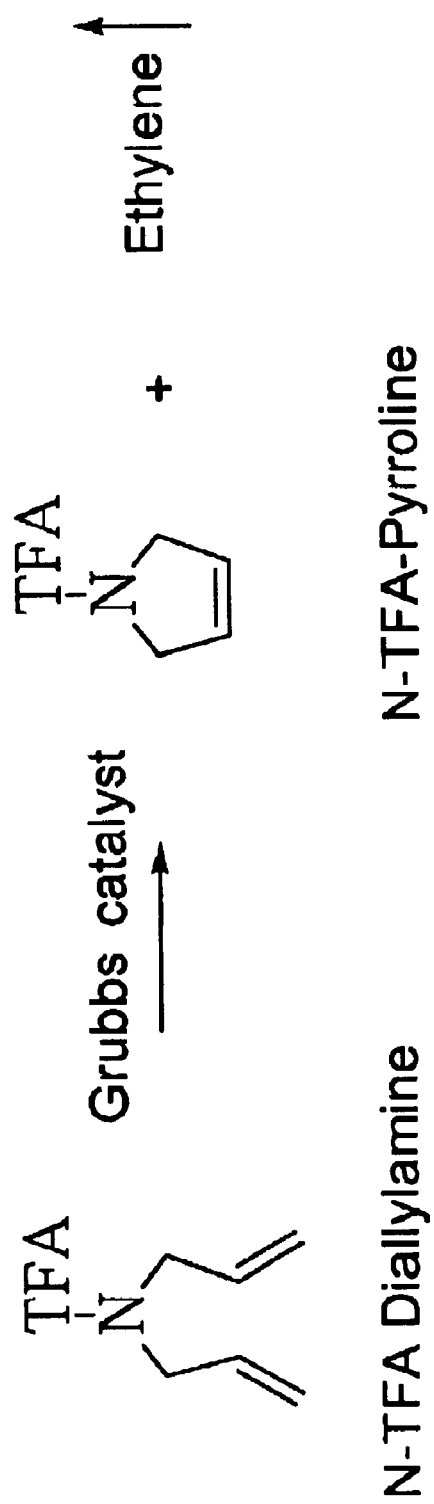
FIG. 9 is a depiction of a metathesis reaction.

Synthesis of TFA-Protected Pyrroline: by Ring-Closing Metathesis of N-TFA Diallylamine The reaction is shown in FIG. 9. To a dry 500-mL round-bottomed flask was added 100.0 g (0.52 mol) of neat N-trifluoroacetyl (TFA) diallylamine and a magnetic stir bar. The solution was cooled to 10° C. and sparged with nitrogen for 20 minutes. Grubbs catalyst 848] 4.4 g (5.2 mmol) was added and the reaction was stirred at 0° C. to 5° C., under 10 mmHg vacuum, for 18 hours. The reaction was quenched with 75 ml of 2M THP in IPA, warmed to 60° C. for 12 hours. Water (100 mL) was added and stirred vigorously for 30 minutes. The aqueous layer was separated, and the product washed with brine solution and dried over sodium sulfate. GC analysis of the reaction mixture indicated 82% N-TFA pyrroline and 18% N-TFA diallylamine.

It will be clear to those having skill in the art who have read this disclosure that many changes may be made to the details of the above-described embodiments of this invention without departing from the underlying principles thereof. The scope of the present invention should, therefore, be determined only by the following claims.

We claim:

1. An olefin metathesis reaction mixture comprising:
   reactants comprising an internal olefin;
   an olefin metathesis catalyst; and
   a metathesis reaction product of an olefin metathesis reaction between the reactants;
   wherein the reaction mixture is maintained at a temperature in the range from about −72° C. to about 14° C. when the olefin metathesis reaction producing the metathesis reaction product proceeds, and wherein rates of reactions other than the olefin metathesis reaction are reduced by temperature conditions to reduce impurity production.

2. The olefin metathesis reaction mixture of claim 1, wherein the olefin metathesis catalyst comprises a Grubbs catalyst.

3. The olefin metathesis reaction mixture of claim 1, wherein the olefin metathesis catalyst comprises a bis phosphine catalyst.

4. The olefin metathesis reaction mixture of claim 1, wherein the olefin metathesis catalyst comprises sIMes or IMes.

5. The olefin metathesis reaction mixture of claim 2, wherein the temperature is in the range from about −5° C. to about 10° C.

6. The olefin metathesis reaction mixture of claim 2, wherein at termination of reaction, the percent yield of metathesis reaction product is within about 0 to about 5 percent of the calculated theoretical yield.

7. The olefin metathesis reaction mixture of claim 2, wherein the metathesis reaction is selected from ring opening reactions and at reaction termination, the percent yield of metathesis reaction product is within about 0 to about 5% of the calculated theoretical yield.

8. The olefin metathesis reaction mixture of claim 3, wherein the temperature is in the range from about 0° C. to about 14° C.

9. The olefin metathesis reaction mixture of claim 3, wherein at termination of reaction, the percent yield of metathesis reaction product is within about 0 to about 5% of calculated theoretical yield.

10. The olefin metathesis reaction mixture of claim 3, wherein the olefin metathesis reaction is selected from ring opening reactions and at reaction termination, the percent yield of metathesis reaction product is within about 0 to about 5% of calculated theoretical yield.

11. The olefin metathesis reaction mixture of claim 4, wherein the temperature is in the range from about −5° C. to about 10° C.

12. The olefin metathesis reaction mixture of claim 4, wherein at termination of reaction, the percent yield of metathesis reaction product is within about 0 to about 5% of calculated theoretical yield.

13. The olefin metathesis reaction mixture of claim 4, wherein the olefin metathesis reaction is selected from ring opening reactions and at reaction termination, the percent yield of metathesis reaction product is within about 0 to about 5% of calculated theoretical yield.

14. A process for olefin metathesis comprising:
selecting an internal olefin;
selecting an olefin metathesis catalyst;
reacting a reaction mixture comprising the internal olefin and the olefin metathesis catalyst, at a temperature in the range from about −72° C. to about 20° C. to produce a selected metathesis reaction product, the reaction mixture comprising an insignificant amount of impurities.

15. The process of claim 14, wherein the olefin metathesis catalyst comprises a Grubbs catalyst.

16. The process of claim 15, wherein the temperature is in the range from about −5° C. to about 10° C.

17. The process of claim 16, wherein the olefin metathesis catalyst is a bis phosphine catalyst.

18. The process of claim 17, wherein the temperature is in the range from about 0° C. to about 14° C.

19. The process of claim 14, wherein the olefin metathesis catalyst comprises a sIMes catalyst.

20. The process of claim 19, wherein the temperature is in the range from about −5° C. to about 10° C.

21. An olefin metathesis reaction mixture comprising:
reactants comprising an olefin;
an olefin metathesis catalyst; and
an inhibitor of reactions other than an olefin metathesis reaction in the mixture;
wherein the olefin metathesis reaction is carried out in solvent free environment and when terminated, the amount of impurities in the reaction product is insignificant.

22. The olefin metathesis reaction mixture of claim 21, wherein the inhibitor is selected from the group consisting of quinone, quinone derivatives, halogenated alkanes, and halogenated aromatics.

23. The olefin metathesis reaction mixture of claim 21, wherein the inhibitor is selected from the group of compounds consisting of electrophilic compounds, nucleophilic compounds, metal hydride inhibitors, and antioxidants.

24. The olefin metathesis reaction mixture of claim 21, wherein the inhibitor is selected from the group consisting of: quinone, halogenated quinones, butylated hydroxytoluene, vitamin E, the halogented aromatics and the halogenated alkanes.

25. The olefin metathesis reaction mixture of claim 21, wherein the olefin metathesis reaction mixture is allowed to react at a temperature elevated to above about 35° C.

26. The olefin metathesis reaction mixture of claim 21, wherein when the olefin metathesis reaction terminates, desired reaction product yield is within about 5% of calculated theoretical yield, based on reactant consumed.

27. The olefin metathesis reaction mixture of claim 1, wherein the olefin comprises 5 decene, the olefin metathesis catalyst comprises a Grubbs catalyst, and the metathesis reaction product comprises 5-decenyl acetate.

28. The olefin metathesis reaction mixture of claim 1, wherein the olefin comprises 1,4-diacetoxy-2-butene, the metathesis reaction product comprises 2-heptenyl acetate, and the olefin metathesis catalyst comprises a Grubbs catalyst.

29. The olefin metathesis reaction mixture of claim 1, wherein the olefin comprises 7-octenyl acetate, the olefin metathesis catalyst comprises a Grubbs catalyst and the metathesis reaction product comprises Z-11-hexadecenyl acetate and/or its isomer.

30. The olefin metathesis reaction mixture of claim 1, wherein the olefin comprises 7-octenyl acetate, the olefin metathesis catalyst comprises a Grubbs catalyst, and the metathesis reaction product comprises E-11-hexadecenyl acetate and/or its isomer.

31. The olefin metathesis reaction mixture of claim 1, wherein the olefin comprises 1,2-epoxy-5-cyclooctene, the olefin metathesis catalyst comprises a Grubbs catalyst and the metathesis reaction product comprises 7,8-epoxy-2-methyl octadecadiene.

32. The olefin metathesis reaction mixture of claim 1, wherein the metathesis reaction product comprises 7,8-epoxy-2-methyl octadecadiene.

33. The olefin metathesis reaction mixture of claim 1, wherein the olefin metathesis reaction comprises a ring opening reaction, and the metathesis reaction product comprises a terminal olefin.

34. The olefin metathesis reaction mixture of claim 1, wherein the metathesis reaction product comprises 4-tridecenyl acetate.

35. The olefin metathesis reaction mixture of claim 34, wherein the olefin metathesis catalyst comprises a Grubbs catalyst and the olefin comprises 9-octadecene.

36. The olefin metathesis reaction mixture of claim 1, wherein the metathesis reaction product comprises an insect pheromone.

37. The olefin metathesis reaction mixture of claim 1, wherein the olefin metathesis catalyst comprises a ruthenium olefin metathesis catalyst.

38. The process of claim 14, wherein the temperature is in the range from about −50 to about 14° C.

39. The process of claim 14, wherein the olefin metathesis catalyst comprises a ruthenium olefin metathesis catalyst.

40. The olefin metathesis reaction mixture of claim 1, wherein the metathesis reaction product comprises a 2-alkenyl acetate or a 2-alkenyl alcohol.

41. The olefin metathesis reaction mixture of claim 2, wherein the olefin metathesis reaction mixture is heated to a higher temperature to initiate the olefin metathesis reaction before the olefin metathesis reaction mixture is maintained at a lower temperature.

42. The olefin metathesis reaction mixture of claim 41, wherein the higher temperature is at least 35° C.

43. The olefin metathesis reaction mixture of claim 1, wherein the reactants comprise at least two different internal olefins.

44. The olefin metathesis reaction mixture of claim 1, wherein a byproduct inhibitor is added to the olefin metathesis reaction mixture, the olefin metathesis reaction occurs under neat conditions, and the byproduct inhibitor is selected from metal hydride inhibitors or antioxidants.

45. The process of claim 14, wherein the olefin metathesis reaction mixture is heated to a higher temperature to initiate the olefin metathesis reaction before the olefin metathesis reaction mixture is maintained at a lower temperature.

46. The process of claim 45, wherein the higher temperature is at least 35° C.

47. The process of claim 14, wherein the reactants comprise at least two different internal olefins.

48. The process of claim 14, wherein a byproduct inhibitor is added to the olefin metathesis reaction mixture, the olefin metathesis reaction occurs under neat conditions, and the byproduct inhibitor is selected from metal hydride inhibitors or antioxidants.

* * * * *